United States Patent
Kim et al.

(10) Patent No.: US 12,112,481 B2
(45) Date of Patent: Oct. 8, 2024

(54) SIMULTANEOUS IMPLEMENTATION METHOD OF 3D SUBTRACTION ARTERIOGRAPHY, 3D SUBTRACTION VENOGRAPHY, AND 4D COLOR ANGIOGRAPHY THROUGH POST-PROCESSING OF IMAGE INFORMATION OF 4D MAGNETIC RESONANCE ANGIOGRAPHY, AND MEDICAL IMAGING SYSTEM

(71) Applicants: THE CATHOLIC UNIVERSITY OF KOREA INDUSTRY-ACADEMIC COOPERATION FOUNDATION, Seoul (KR); KONKUK UNIVERSITY GLOCAL INDUSTRY-ACADEMIC COLLABORATION FOUNDATION, Chungcheongbuk-do (KR)

(72) Inventors: Hyun Jeong Kim, Daejeon (KR); Hong Gee Roh, Seoul (KR)

(73) Assignees: THE CATHOLIC UNIVERSITY OF KOREA INDUSTRY-ACADEMIC COOPERATION FOUNDATION, Seoul (KR); KONKUK UNIVERSITY GLOCAL INDUSTRY-ACADEMIC COLLABORATION FOUNDATION, Chungcheongbuk-Do (KR)

(*) Notice: Subject to any disclaimer, the term of this patent is extended or adjusted under 35 U.S.C. 154(b) by 495 days.

(21) Appl. No.: 17/625,911

(22) PCT Filed: Mar. 18, 2020

(86) PCT No.: PCT/KR2020/003686
§ 371 (c)(1),
(2) Date: May 19, 2022

(87) PCT Pub. No.: WO2021/006460
PCT Pub. Date: Jan. 14, 2021

(65) Prior Publication Data
US 2023/0186474 A1    Jun. 15, 2023

(30) Foreign Application Priority Data

Jul. 11, 2019   (KR) .................. 10-2019-0083920

(51) Int. Cl.
G06T 7/00    (2017.01)
A61B 5/055   (2006.01)
G06T 19/20   (2011.01)

(52) U.S. Cl.
CPC .......... *G06T 7/0016* (2013.01); *A61B 5/055* (2013.01); *G06T 19/20* (2013.01);
(Continued)

(58) Field of Classification Search
None
See application file for complete search history.

(56) References Cited

U.S. PATENT DOCUMENTS

| | | | | |
|---|---|---|---|---|
| 6,018,600 A | * | 1/2000 | Levin ................. | G01R 33/561 382/284 |
| 6,567,567 B1 | * | 5/2003 | Levin ................. | G01R 33/561 382/128 |

(Continued)

FOREIGN PATENT DOCUMENTS

| | | |
|---|---|---|
| KR | 10-2014-0142652 A | 12/2014 |
| KR | 10-2017-0092903 A | 8/2017 |
| KR | 10-1885998 B1 | 8/2018 |
| WO | WO 2005/106517 A2 | 11/2005 |

OTHER PUBLICATIONS

International Search Report for PCT/KR2020/003686 mailed on Jul. 21, 2020.

*Primary Examiner* — Anand P Bhatnagar
(74) *Attorney, Agent, or Firm* — The PL Law Group, PLLC

(57) ABSTRACT

A simultaneous implementation method of 3D subtraction magnetic resonance (MR) arteriography, 3D subtraction MR venography, and color-coded 4D MR angiography through post-processing of image information of 4D MR angiography according to an embodiment of the present disclosure may reduce scan time required to individually obtain an MR (Continued)

arteriography and an MR venography. In addition, not only anatomical information of arteries but also more accurate anatomical information of veins and more detailed hemodynamic information may be obtained.

9 Claims, 25 Drawing Sheets

(52) U.S. Cl.
CPC ............................ *G06T 2200/04* (2013.01); *G06T 2207/10076* (2013.01); *G06T 2207/10088* (2013.01); *G06T 2207/20092* (2013.01); *G06T 2207/20132* (2013.01); *G06T 2207/20224* (2013.01); *G06T 2207/30096* (2013.01); *G06T 2207/30101* (2013.01); *G06T 2219/2012* (2013.01)

(56) References Cited

U.S. PATENT DOCUMENTS

| | | | | |
|---|---|---|---|---|
| 7,467,006 | B2* | 12/2008 | Abe | G01R 33/5601 |
| | | | | 324/309 |
| 8,781,197 | B2* | 7/2014 | Wang | G01R 33/54 |
| | | | | 382/131 |
| 9,404,986 | B2* | 8/2016 | White | G01R 33/48 |
| 9,572,514 | B2* | 2/2017 | Wang | G01R 33/5614 |
| 11,890,086 | B2* | 2/2024 | Wang | G01R 33/561 |
| 2007/0078333 | A1* | 4/2007 | Abe | G01R 33/5601 |
| | | | | 600/420 |
| 2011/0044524 | A1* | 2/2011 | Wang | G01R 33/5601 |
| | | | | 382/131 |
| 2016/0314581 | A1* | 10/2016 | Contini | G06T 7/0012 |
| 2017/0332936 | A1* | 11/2017 | Wang | G01R 33/4824 |
| 2018/0032653 | A1* | 2/2018 | Aben | A61B 6/032 |
| 2019/0015061 | A1 | 1/2019 | Liebeskind et al. | |
| 2020/0222018 | A1* | 7/2020 | van Walsum | A61B 6/463 |
| 2021/0035290 | A1* | 2/2021 | Aben | G06T 7/344 |
| 2021/0137634 | A1* | 5/2021 | Lang | A61B 34/20 |
| 2023/0346507 | A1* | 11/2023 | Lang | A61B 90/96 |

* cited by examiner

SIMULTANEOUS IMPLEMENTATION METHOD OF 3D SUBTRACTION ARTERIOGRAPHY, 3D SUBTRACTION VENOGRAPHY, AND 4D COLOR ANGIOGRAPHY THROUGH POST-PROCESSING OF IMAGE INFORMATION OF 4D MAGNETIC RESONANCE ANGIOGRAPHY, AND MEDICAL IMAGING SYSTEM

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2020/003686, filed Mar. 18, 2020, which claims priority to the benefit of Korean Patent Application No. 10-2019-0083920 filed in the Korean Intellectual Property Office on Jul. 11, 2019, the entire contents of which are incorporated herein by reference.

BACKGROUND

1. Technical Field

The present disclosure relates to post-processing of magnetic resonance (MR) angiography images, and more particularly, to a simultaneous implementation method of 3D subtraction MR arteriography, 3D subtraction MR venography, and color-coded 4D MR angiography through post-processing of image information of the 4D MR angiography, and a medical imaging system.

2. Background Art

Medical imaging devices mainly used for cerebrovascular diseases include Magnetic Resonance Imaging (MRI), Computed Tomography (CT), Single Photon Emission Computed Tomography (SPECT), Positron Emission Tomography (PET) and Ultrasound. Among them, CT and MRI are widely used to identify cerebral blood vessel lesions. Because cerebrovascular diseases have diverse causes and treatment methods and prognosis of the cerebrovascular diseases may vary depending on patients, imaging diagnosis play a very important role in analyzing exact causes and determining appropriate treatment methods and various imaging techniques have been developed and used. Examples of imaging techniques currently being developed and used include Time-of-Flight (TOF) MR arteriography, Phase-contrast (PC) MR arteriography, TOF MR venography, PC MR venography, Contrast-enhanced TOF MR venography, Contrast-Enhanced 3D fast gradient-echo MR arteriography, Contrast-Enhanced 3D fast gradient-echo MR venography, 4D Dynamic contrast-enhanced MR angiography, Contrast-Enhanced 3D or 4D CT angiography, and Contrast-Enhanced 3D CT venography.

Cerebrovascular diseases may be caused by diseases of veins as well as arteries. Although most acute strokes are caused by abnormalities in the arteries, about 1 to 3% of acute strokes are caused by abnormalities in veins. Thus, it may be necessary to evaluate both arteries and veins. In order to obtain both MR arteriography and MR venography using conventional methods, it takes a relatively long time, which is typically 7 to 10 minutes or more. Such a long period of time brings discomfort to patients, and, in particular, motion artifacts caused by movement are more likely to occur in patients with cerebrovascular disease who are highly likely to be unconscious.

Existing imaging methods for viewing only arteries are relatively well developed, and thus well show lesions as well as anatomical structures. However, imaging methods for viewing veins are still not satisfactory. In particular, in typical MR venography using TOF or PC techniques, which are most commonly used, the image quality is very often unsatisfactory due to various types of artifacts.—Contamination of arterial signals often occurs, and there is a limitation in visualizing small veins such as cortical veins or veins with slow flow. Contrast-enhanced 3D fast gradient-echo MR venography is sometimes used to partially overcome this limitation, but it is not easy to obtain at an appropriate time and contamination by arterial signals are common.

In conclusion, in cerebrovascular diseases that require rapid diagnosis and treatment, in particular, acute stroke or similar situations, decision-making and treatment may be delayed due to long examination time and unsatisfactory images.

Furthermore, in most cases, conventional MR arteriography and conventional MR venography display only static images without hemodynamic information despite a long examination time. However, 4D MR angiography used in the present disclosure provides hemodynamic information along with vascular anatomy in a short scan time of about 1 minute. However, it cannot show arteries and veins separately, so a solution is needed.

SUMMARY

Provided are a method of simultaneously implementing magnetic resonance (MR) arteriography and improved-quality MR venography which have to be obtained separately by conventional methods, while creating a color-coded 4D magnetic MR angiography emphasizing the dynamics of 4D MR angiography characterized by a multiphase, through post-processing of 4D MR angiography image data, and a medical imaging system.

According to an aspect of the present disclosure, a simultaneous implementation method of three-dimensional (3D) subtraction magnetic resonance (MR) arteriography, 3D subtraction MR venography, and color-coded four-dimensional (4D) MR angiography through post-processing of image information of 4D MR angiography includes a first operation of, when a time unit for generating and processing 4D MR angiography images is a phase, loading 4D MR angiography image data obtained repeatedly from the aortic arch to the top of the head for each phase, extracting an entire region or a necessary region, and storing the extracted region as a file having entire image information including time, space, and signal intensity information; a second operation of opening the stored file to output subtraction maximum intensity projection (MIP) images arranged in a time order, and checking whether 4D MR angiography images are arranged in a time order; a third operation of generating time-intensity curves of the artery and vein that change according to the concentration and flow of a contrast medium, by designating optimal regions of interest (ROIs) on the M1 segment of the middle cerebral artery and the superior sagittal sinus, and determining an arterial phase, a capillary phase, and a venous phase; a fourth operation of color-coding all blood vessels in different colors according to phases when the blood vessels begin to appear and changes of the signal intensity, after processes of dividing blood vessel image information according to the arterial phase, the capillary phase, and the venous phase, extracting only an artery signal by subtracting venous phase image information from arterial phase image information, and extracting only a vein signal by subtracting arterial phase image information from venous phase image information; and a fifth operation of storing and outputting image information of 3D subtraction MR arteriography and 3D subtraction MR venography generated in the fourth operation as a grayscale and a color scale, and storing and outputting a color-coded 4D MR angiography image, in which entire hemodynamic information of a 4D MR angiography image is emphasized, and a color-coded 3D MR angiography image.

To obtain an angiographic image of a specific region in this process, the first operation may further include an operation of opening a cropping window to remove unnecessary portions from the entire field of view, designating only a desired region, and storing angiographic image files of the specific region.

In the fourth operation, arterial phase blood vessels from a time point when the arterial signal starts to rise to the arterial peak phase when the arterial signal intensity is greatest may be displayed in red, venous phase blood vessels from the venous peak phase when the venous signal intensity is greatest to a time point when the venous signal decreases and reaches a plateau may be displayed in blue, and a blood vessels between the arterial peak phase and the venous peak phase may be displayed in green. Color weightings of red, blue, and green may be adjusted according to the signal intensity so that blood vessels of a desired phase and dynamic changes are more visible, to thereby implement color MR angiography.

In the simultaneous implementation method of 3D subtraction MR arteriography, 3D subtraction MR venography, and color-coded 4D MR angiography through post-processing of image information of 4D MR angiography, an arterial mask only having a value greater than or equal to 0 may be created by subtracting a venous phase signal from an arterial phase signal, and then arterial phase MIP is multiplied by the arterial mask to obtain 3D subtraction MR arteriography, and a venous mask only having a value greater than or equal to 0 may be created by subtracting an arterial phase signal from a venous phase signal, and then venous phase MIP is multiplied by the venous mask to obtain 3D subtraction MR venography. The simultaneous implementation method may further include, in order to obtain a projection in which a lesion or a specific blood vessel is well visible, designating various angles around x, y, and z axes, rotating an image, and checking and processing an updated display; and obtaining and storing continuous images rotated at a certain angle designated by a user, based on the x axis or the z axis. The simultaneous implementation method may further include storing all images obtained in the present disclosure in a standard medical image format (Dicom image format).

According to the technical aspect of the present disclosure, a medical imaging system for simultaneously implementing 3D subtraction MR arteriography, 3D subtraction MR venography, and color-coded 4D MR angiography through post-processing of image information of 4D MR angiography includes an input interface configured to receive, as an input, 4D MR angiography image data obtained repeatedly from the aortic arch to the top of the head at intervals of a predetermined time; an extractor configured to cut out an entire portion or a desired portion from the 4D MR angiography image data, and store the cut-out portion as a file including both information about the shape and location of blood vessels and information about changes in blood flow and signal intensity according to time; a phase setter configured to output the 4D MR angiography image as subtraction maximum intensity projection (MIP) images arranged in a time order, designate regions of interest (ROIs) on the M1 segment of the middle cerebral artery (MCA) and the superior sagittal sinus (SSS), based on the subtraction MIP images to create time-intensity curves of the cerebral artery and cerebral vein, and then classify an arterial phase, a capillary phase, and a venous phase; a subtraction image processor configured to generate subtraction MR arteriography images and a subtraction MR venography images by distinguishing and calculating blood vessels from a time point when the arterial signal starts to rise to the arterial peak phase when the arterial signal intensity is greatest, blood vessels from the venous peak phase when a signal intensity of vein is greatest to a time point when the venous signal decreases and reaches to a plateau, and blood vessel image information between the arterial peak phase and the venous peak phase; a color coding unit configured to classify blood vessels of a 3D subtraction MR arteriography image, a 3D subtraction MR venography image, and a 4D MR angiography image into arteries, capillaries, and veins according to phases when the blood vessels are seen, and distinguish the arteries, the capillaries, and the veins in different colors; and an image output interface configured to output and store a 3D subtraction MR arteriography image including only arteries, a 3D subtraction MR venography image including only veins, and a color-coded 4D MR angiography image.

The subtraction image processor may include an MR arteriography subtractor configured to subtract venous phase signals from arterial phase signals for each pixel to create an arterial mask having a value greater than or equal to 0, and update an arterial phase MIP by multiplying the arterial phase MIP by the arterial mask to obtain 3D subtraction MR arteriography; and an MR venography subtractor configured to subtract arterial phase signals from venous phase signal for each pixel to create a venous mask only having a value greater than or equal to 0, and update a venous phase MIP by multiplying the venous phase MIP by the venous mask to obtain 3D subtraction MR venography.

The color coding unit may include a color weighting adjuster configured to allow an arterial phase blood vessels from a time point when the arterial signal starts to rise to the arterial peak phase when the arterial signal intensity is greatest to be displayed in red, allow venous phase blood vessels from a the venous peak phase when the venous signal intensity is greatest to a time point when the venous signal decreases and reaches to a plateau to be displayed in blue, allow blood vessels between the arterial peak phase and the venous peak phase to be displayed in green, and adjust color weightings of red, blue, and green in order to make blood vessels of a desired phase and hemodynamic changes more visible, and set an optimal value that may vary depending on differences in MRI machines, imaging methods or contrast enhancement degrees.

The image output interface may include a SUB MR arteriography image output interface configured to output and store grayscale and color 3D subtraction MR arteriography images; a SUB MR venography image output interface configured to output and store grayscale and color 3D subtraction MR venography images; a color-coded 4D MR angiography image output interface configured to output and store a color-coded 4D MR angiography image and a color-coded 3D MR angiography image; and an image rotator configured to freely rotate an angiographic image about x, y, and z axes to obtain a projection in which a lesion or a specific blood vessel is well visible, or obtain continuous images rotated at a constant angle about the x and z axes.

In a simultaneous implementation method of 3D subtraction magnetic resonance (MR) arteriography, 3D subtraction MR venography, and color-coded 4D MR angiography through post-processing of image information of 4D MR angiography, and a medical imaging system, according to the present disclosure, contamination of images due to veins or arteries is removed by using multi-phase characteristics of 4D MR angiography and a subtraction technique and a color-coding technique to thereby obtain a subtraction MR arteriography image showing only arteries and a subtraction MR venography image showing only veins, and color 3D subtraction MR arteriography and color 3D subtraction MR venography images, and color-coded 4D MR angiography and color-coded 3D MR angiography images for easy viewing of overall hemodynamic information may also be obtained through 3D reconstruction and coloring for easy visual identification.

In other words, an arterial phase, a capillary phase, and a venous phase of 4D MR angiography may be accurately determined according to the hemodynamic characteristics of each patient, and information on the arteries and information on the veins may be accurately separated by using a subtraction technique, so that only arteries or veins may be selectively extracted and expressed. This prevents complex appearance of arteries and veins overlapping each other and enables easy anatomical evaluation.

In particular, in conventional MR venography, connection of venous blood vessels is cut off due to many artifacts, small or slow-flowing veins are not visible, or information on arteries is mixed, in many cases. However, according to the present disclosure, loss of vascular information of small veins such as cortical veins and veins with slow blood flow is minimized through a contrast enhancement effect and removal of arteries, and anatomical expression of veins is more accurate, leading to a significant improvement in the quality of MR venography.

In addition, conventional 4D MR angiography has a disadvantage in that it is not easy to visually separate arteries from veins because a complex blood vessel structure is expressed only in grayscale. However, according to the present disclosure, color-coded 4D MR angiography and color-coded 3D MR angiography both emphasizing hemodynamic information are implemented by differentiating colors according to the phases when blood vessels appear, and thus complex blood vessel structures and hemodynamic characteristics may be easily visually ascertained.

According to the present disclosure, scan time required to individually obtain an MR arteriography and an MR venography by using various existing methods are significantly reduced, and still not only anatomical information of arteries but also more accurate anatomical information of veins and more detailed hemodynamic information may be obtained. In other words, it takes a long time (3 to 7 minutes) to obtain each of conventional MR arteriography and conventional MR venography, but, in the present disclosure, 3D MR arteriography and 3D MR venography are simultaneously implemented with 4D MR angiography obtained in only 1 to 2 minutes, leading to a great reduction in overall scan time. In particular, the present disclosure is advantageous in securing the golden time required to treat acute cerebrovascular disease patients who require urgent care, and enables decision-making necessary for treatment to be more accurate and quick, and a quality MR venography image enables easy detection and treatment of venous cerebrovascular diseases.

DETAILED DESCRIPTION

The prevent disclosure will now be described more fully with reference to the accompanying drawings, in which exemplary embodiments are shown. Configurations illustrated in the embodiments and the drawings described in the present specification are only the most preferred embodiment of the present disclosure and do not represent all of the technical spirit of the present disclosure, and thus it is to be understood that various equivalents and modified examples, which may replace the configurations, are possible when filing the present application.

Figure 1:
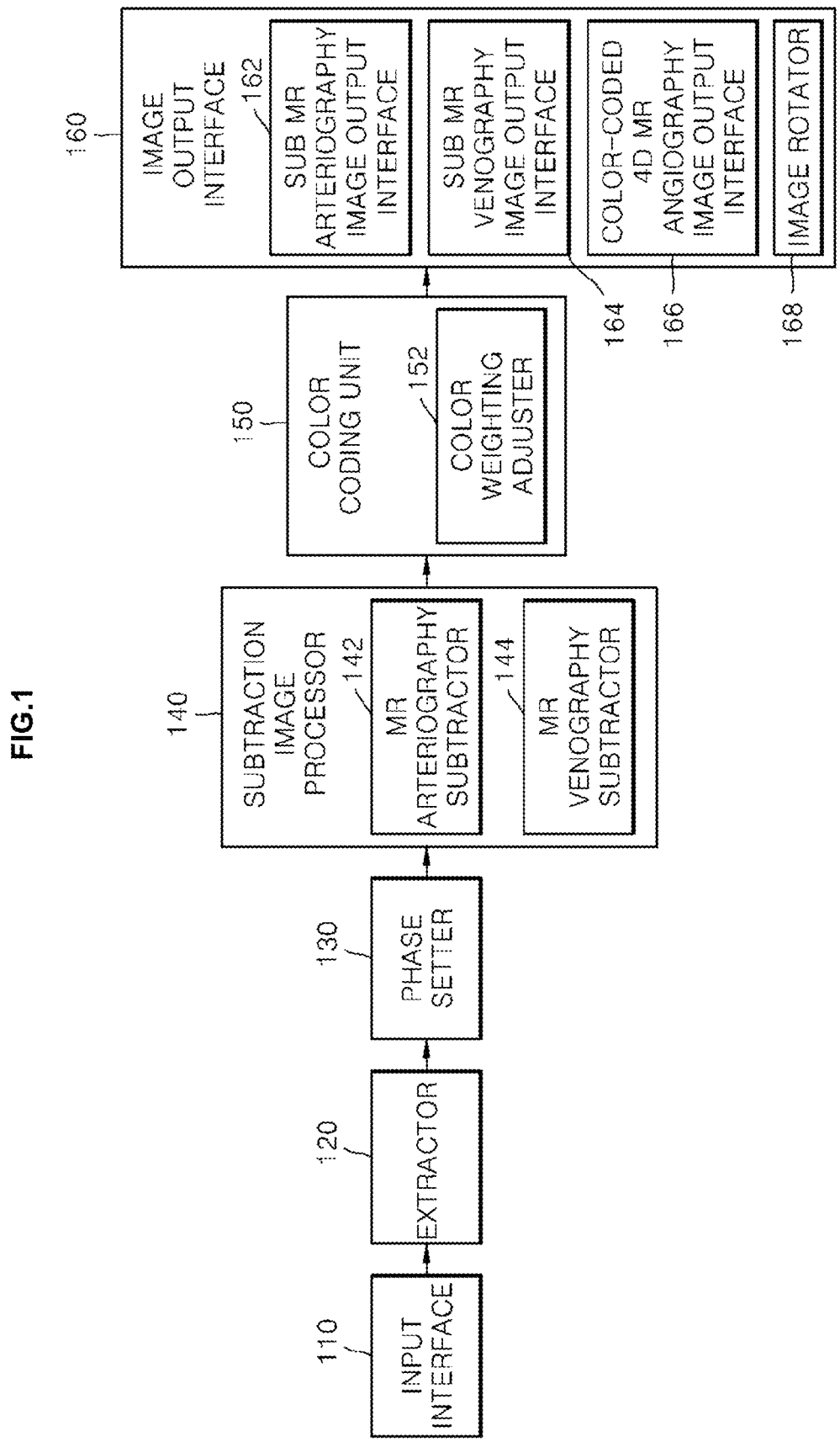
FIG. 1 is a block diagram of a medical imaging system for simultaneously implementing 3D subtraction magnetic resonance (MR) arteriography, 3D subtraction MR venography, and color-coded 4D MR angiography through image information post-processing of 4D MR angiography, according to an embodiment of the present disclosure.

FIG. 1 is a block diagram of a medical imaging system for simultaneously implementing 3D subtraction magnetic resonance (MR) arteriography, 3D subtraction MR venography, and color-coded 4D MR angiography through image information post-processing of 4D MR angiography, according to any embodiment of the present disclosure. The medical imaging system includes an input interface 110, an extractor 120, a phase setter 130, a subtraction image processor 140, a color coding unit 150, and an image output interface 160.

The input interface 110 receives, as an input, 4D MR angiography image data obtained repeatedly from the aortic arch to the top of the head at intervals of a predetermined time, for example, at intervals of a short period of time within 2.5 seconds.

The extractor 120 cuts out the entire portion or a desired portion from the 4D MR angiography image data received as the input, and stores the entire or cut-out portion as a file including both information about the shape and location of blood vessels and information about changes in blood flow and signal intensity according to time.

The phase setter 130 outputs the 4D MR angiography image as subtraction maximum intensity projection (MIP) images arranged in a time order, and designates regions of interest (ROIs) on the M1 segment of the middle cerebral artery (MCA) and the superior sagittal sinus (SSS), based on the subtraction MIP images, to thereby create time-intensity curves of the cerebral artery and cerebral vein according to time. Then, the phase setter 130 sets an arterial phase, a capillary phase, and a venous phase, based on the time-intensity curves.

The subtraction image processor 140 generates a subtraction MR arteriography image and a subtraction MR venography image by distinguishing and calculating a blood vessels from a time point when the arterial signal starts to rise to the arterial peak phase and a blood vessels from the venous peak phase to a time point when a the venous signal decreases to a plateau and blood vessel image information between the arterial peak phase and the venous peak phase, and includes an MR arteriography subtractor 142 and an MR venography subtractor 144.

The MR arteriography subtractor 142 subtracts a venous phase signal from an arterial phase signal to create an arterial mask having a value greater than or equal to 0, and updates an arterial phase MIP by multiplying the arterial phase MIP by the arterial mask to obtain 3D subtraction MR arteriography.

The MR venography subtractor 144 subtracts an arterial phase signal from a venous phase signal to create a venous mask only having a value greater than or equal to 0, and updates a venous phase MIP by multiplying the venous phase MIP by the venous mask to obtain 3D subtraction MR venography.

The color coding unit 150 may distinguish subtracted arteriography image information and subtracted venography image information and all phases of 4D MR angiography in different colors according to time, and may include a color weighting adjuster 152. The color coding unit 150 may allow arterial phase blood vessels from a time point when the arterial signal starts to rise to the arterial peak phase to be displayed in red, allow venous phase blood vessels from the venous peak phase to a time point when the venous signal decreases to a plateau to be displayed in blue, and allow capillary phase blood vessels between the arterial peak phase and the venous peak phase to be displayed in green. The color weighting adjuster 152 may adjust color weightings of red, blue, and green in order to make blood vessels of a desired phase and hemodynamic changes more visible, and may set an optimal value according to differences in MRI machines, imaging methods, or contrast enhancement degrees.

The image output interface 160 outputs and stores a 3D subtraction MR arteriography image including only arteries, a 3D subtraction MR venography image including only veins, and a color-coded 4D MR angiography image, and includes a SUB MR arteriography image output interface 162, a SUB MR venography image output interface 164, a color-coded 4D MR angiography image output interface 166, and an image rotator 168. The SUB MR arteriography image output interface 162 outputs and stores grayscale and color 3D subtraction MR arteriography images. The SUB MR venography image output interface 164 outputs and stores grayscale and color 3D subtraction MR venography images. The color-coded 4D MR angiography image output interface 166 outputs and stores a color-coded 4D MR angiography image and a color-coded 3D MR angiography image. The image rotator 168 may freely rotate each angiographic image about x, y, and z axes to obtain a projection in which a lesion or a specific blood vessel is well visible, or may obtain continuous images rotated at a constant angle about the x and z axes.

Figure 2:
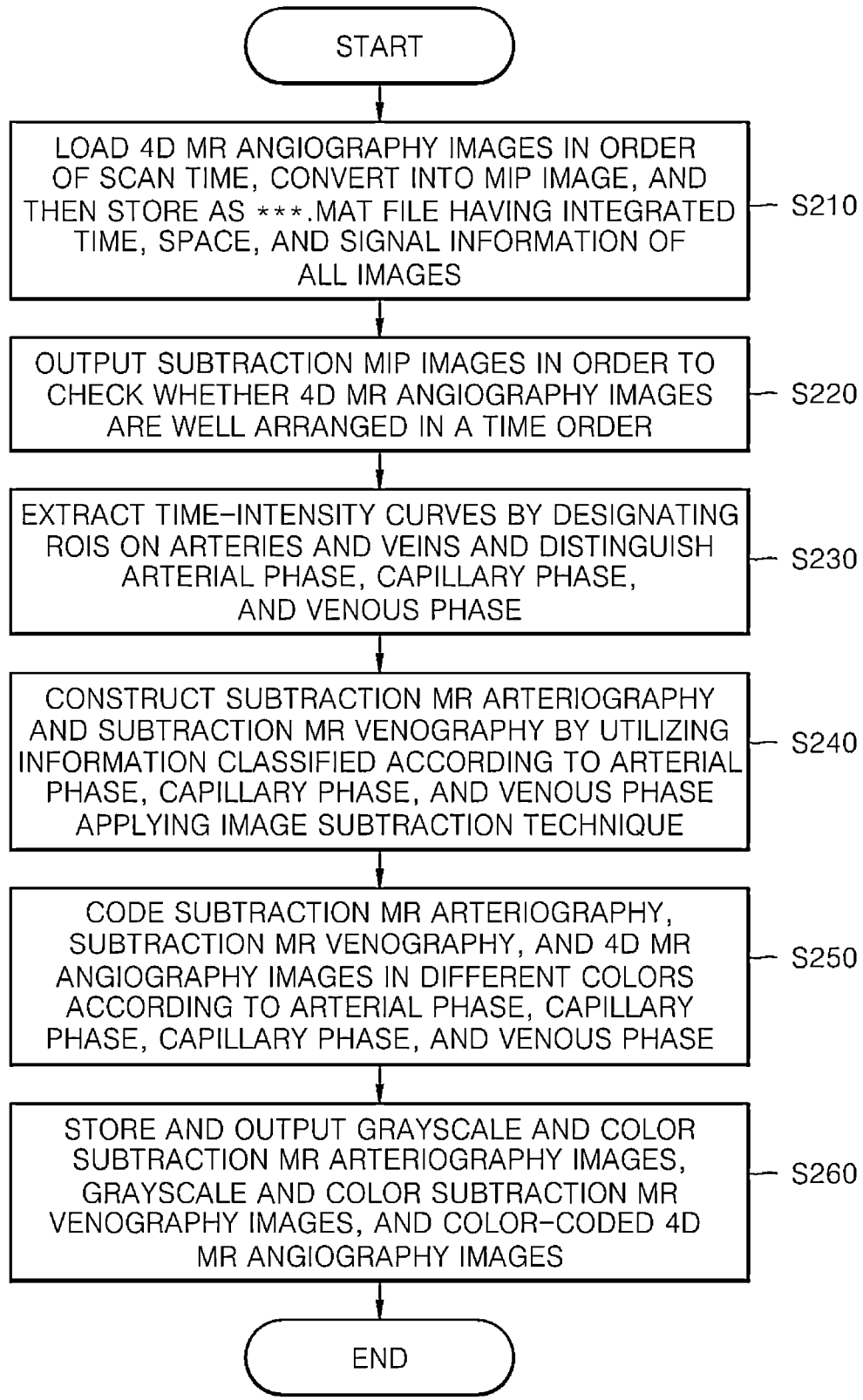
FIG. 2 is a flowchart of a method of simultaneously implementing 3D subtraction MR arteriography, 3D subtraction MR venography, and color-coded 4D MR angiography through image information post-processing of 4D MR angiography, according to an embodiment of the present disclosure.

FIG. 2 is a flowchart of a method of simultaneously implementing 3D subtraction MR arteriography, 3D subtraction MR venography, and color-coded 4D MR angiography through image information post-processing of 4D MR angiography, according to an embodiment of the present disclosure. A method of a method of simultaneously implementing 3D subtraction MR arteriography, 3D subtraction MR venography, and color-coded 4D MR angiography through image information post-processing of 4D MR angiography, according to the present disclosure, will now be described with reference to FIG. 2.

First, when a time unit for generating and processing a 4D MR angiography image is a phase, 4D MR angiography images obtained repeatedly from the aortic arch to the top of the head for each phase are loaded in an order of scan time, and the entire region or a necessary region is extracted and stored as a ***.mat file that is a single file having entire image information including time, space, and signal intensity information (operation S210). In this operation, a first phase image not yet subjected to contrast enhancement from among the loaded images is subtracted from the remaining phase images, and thus image information is converted into an MIP form from which background noise has been removed, and is stored. In addition, in order to obtain an angiographic image of a specific region in this process, the method may further include an operation of opening a cropping window to remove unnecessary portions from the entire field of view, designating only a desired region, and storing an angiographic image file of the specific region.

The stored file is open to output subtraction MIP images arranged in a time order, in order to check whether 4D MR angiography images are arranged in a time order (operation S220).

Time-intensity curves of the artery and vein that change according to the concentration of a contrast medium are created by designating ROIs on the M1 segment of the MCA and the SSS, and arterial, capillary, and venous phases are determined and distinguished (operation S230).

A subtraction MR arteriography image and a subtraction MR venography image are constructed through a process of dividing blood vessel image information according to the arterial phase, the capillary phase, and the venous phase, extracting only an artery signal by subtracting venous phase image information from arterial phase image information, and extracting only a vein signal by subtracting arterial phase image information from venous phase image information (operation S240).

Arteries, capillaries, and veins appearing in an 4D MR angiography image may be coded in different colors according to phases when blood vessels are visible, so as to be distinguished from one another (operation S250). For example, blood vessels from a time point when the arterial signal starts to rise to the arterial peak phase are highlighted in red from among RGB (red, green, and blue) and displayed, blood vessels from the venous peak phase to the time point when the venous signal decreases to the plateau are highlighted in blue and displayed, and blood vessels between the arterial peak phase and the venous peak phase are highlighted in green and displayed. In order to express a wash-in/wash-out (blood flow fills in and out) phenomenon of blood vessels, time-intensity curve information of artery and vein is converted into a color-weighting conversion factor, and the color-weighting conversion factor is additionally applied to changes in the colors of arteries (red) and veins (blue) to realize a color 4D MR angiography image in which dynamic changes in blood flow over time have been reflected. In addition, the color weightings of red, blue, and green may be manually adjusted so that blood vessels at a desired time, such as arteries or veins, are more clearly visible.

Color 3D subtraction MR arteriography is generated by adjusting a red weighting corresponding to arteries to be relatively high and then performing color coding on a grayscale 3D subtraction MR arteriography image obtained through operation S240, and color 3D subtraction MR venography is generated by adjusting a blue weighting corresponding to veins to be relatively high and then performing color coding on a grayscale 3D subtraction MR venography image.

Finally, color 3D MR angiography is generated by applying color weightings to grayscale 3D MR angiography in which arteries, capillaries, and veins are all visible, according to the arterial phase (red), the capillary phase (green), and the venous phase (blue).

3D images of subtraction MR arteriography and subtraction MR venography generated in operation S250 are stored and output as grayscale and color images, and a color-coded 4D MR angiography image in which the entire hemodynamic information of a 4D MR angiography image is emphasized, and a color-coded 3D MR angiography image in which pieces of blood flow information of all phases are combined and seen are stored and output (operation S260).

In order to obtain a projection in which a lesion or a specific blood vessel is well visible, an image may be rotated at a user-specified angle around the x, y, and z axes, and an updated display may be checked.

An arterial mask having only a value equal to or greater than 0 may be created by subtracting venous phase signals from arterial phase signals, subtraction MR arteriography may be generated by updating an arterial phase MIP by multiplying the arterial phase MIP by the arterial mask, and a venous mask having only a value equal to or greater than 0 may be created by subtracting arterial phase signals from venous phase signals, and subtraction MR venography may be generated by updating a venous phase MIP by multiplying the venous phase MIP by the venous mask, An image rotated around the x-axis or z-axis may be stored, and continuous images rotated at a constant angle may be obtained. All images obtained in the present disclosure may be stored in a standard medical image format (Dicom image format).

FIGS. 3 through 7 are exemplary interfaces for using a program implementing a 4D MR angiography image information post-processing method according to the present disclosure, and illustrate a process of inputting 4D MR angiography data, cutting out the entire portion or a desired portion, and displaying the cut-out portion as subtraction MIP images listed according to phases.

Figure 3:
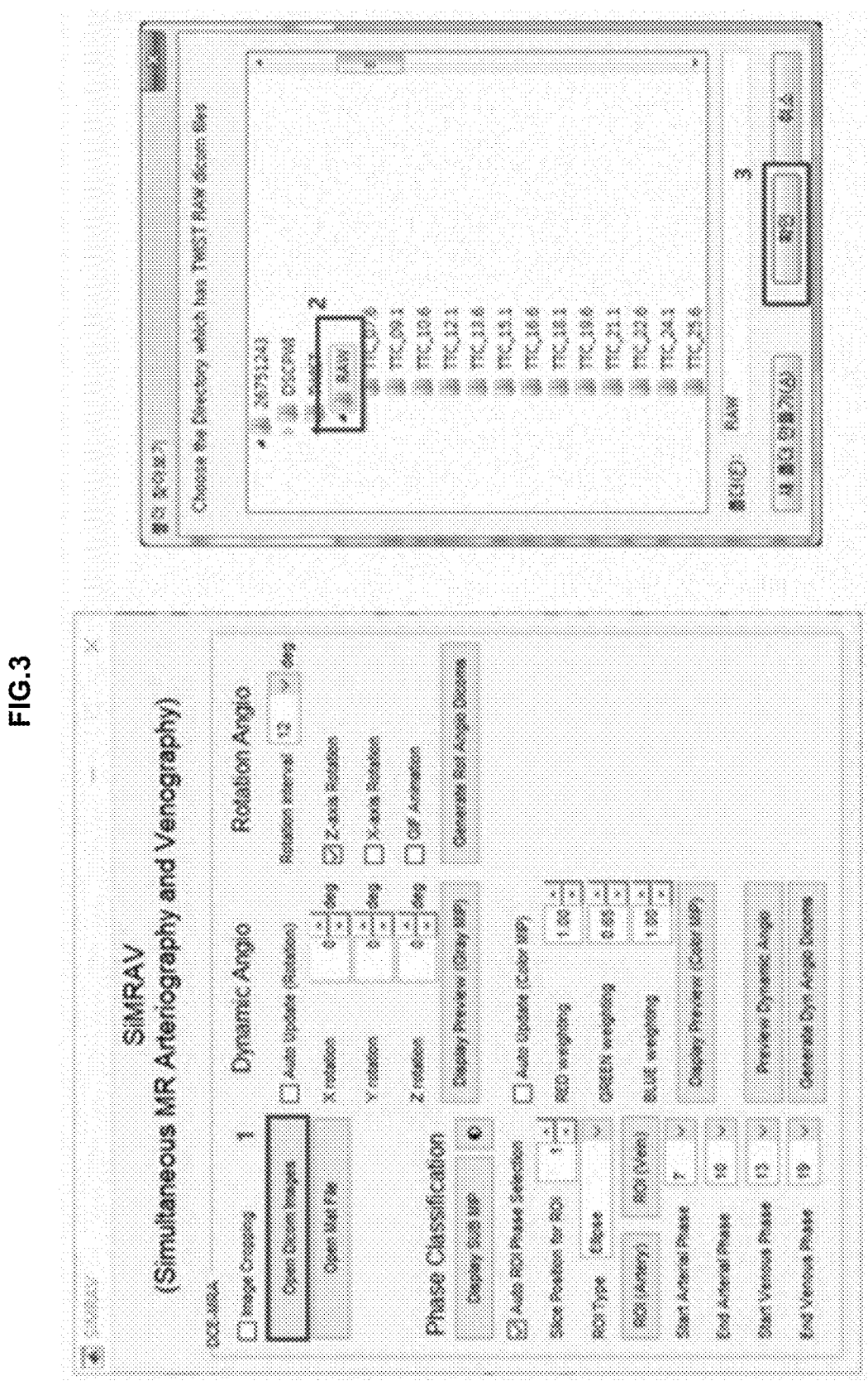
FIGS. 3 through 7 are exemplary interfaces for using a program implementing a 4D MR angiography image information post-processing method according to the present disclosure, and illustrate a process of inputting 4D MR angiography data, cutting out the entire portion or a desired portion, and displaying the cut-out portion as subtraction MIP images listed according to phases.
Figure 4:
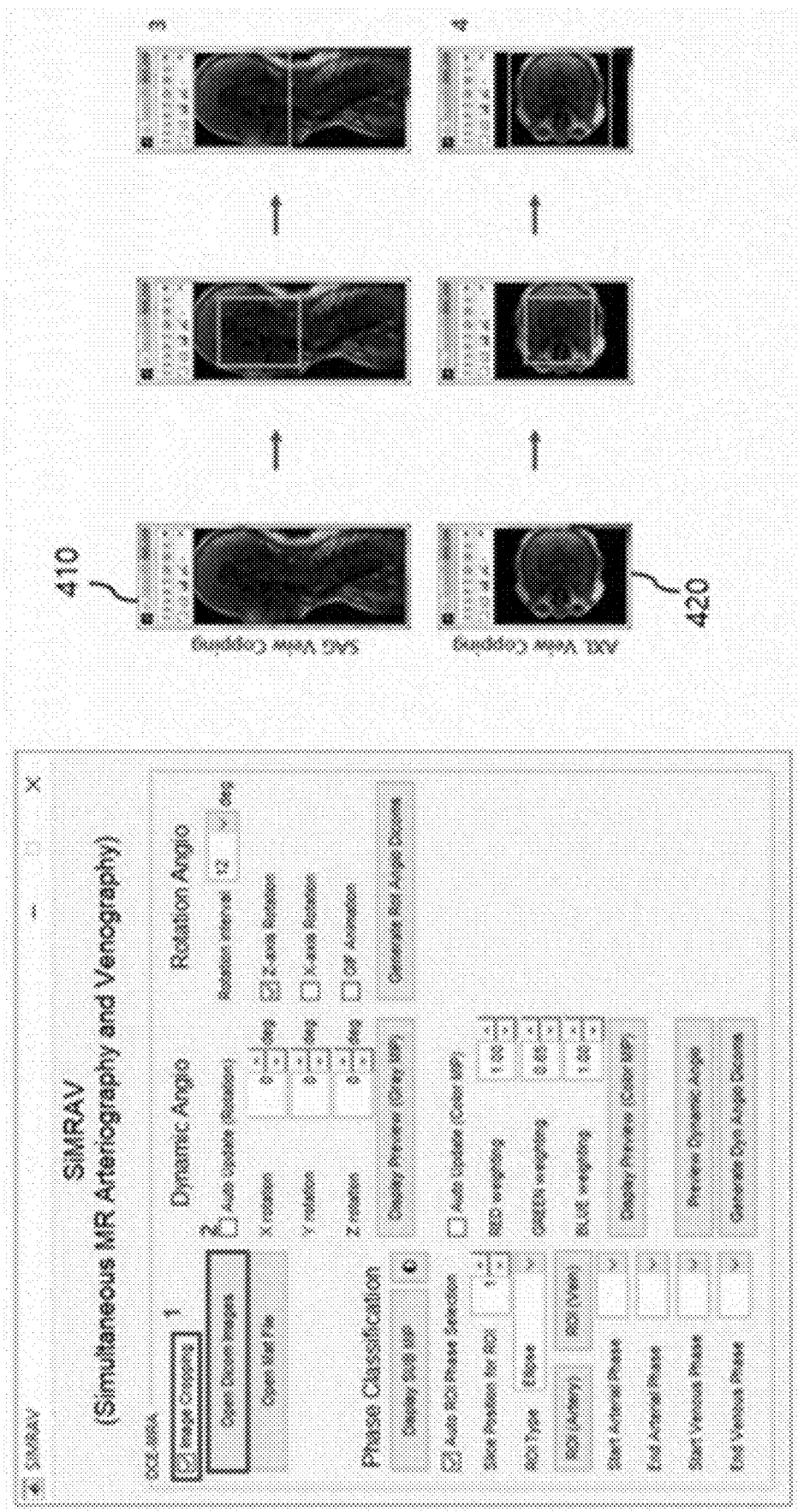

FIGS. 3 and 4 illustrate that, in a medical imaging system according to the present disclosure, a Dicom source image (raw data) is open to make a subtraction MIP image for the entire region or a desired specific region, and the subtraction MIP image is stored as a *.mat file having a signal intensity and spatial and temporal information. In particular, in order to obtain an angiographic image of a specific region, the process may further include an operation of opening a cropping window to remove unnecessary portions as shown in FIG. 4, designating only the specific region to be watched on the entire region, and storing the designated specific region as a *.mat image file having information of only the designated area.

For example, when only angiography of a brain region is obtained, "Cropping (1)" is previously checked, and "Dicom Images (2)" is clicked. A sagittal cropping window 410 and an axial cropping window 420 are automatically open in a stated order, a box of each of the cropping windows is clicked with a left mouse button and dragged to designate only the brain region. Then, only information of the brain region is processed and then a ***.mat file is stored.

Figure 5:
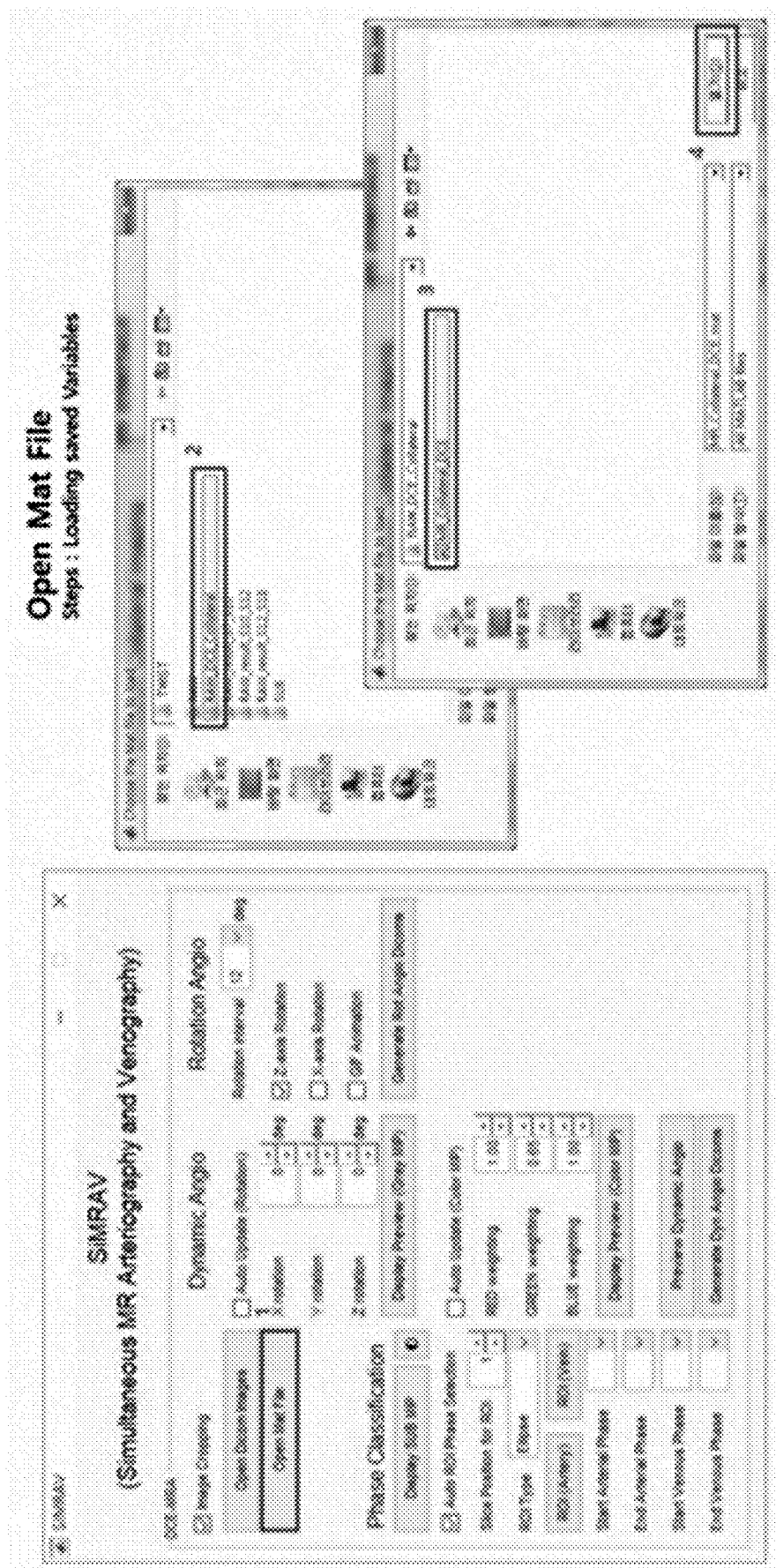

FIG. 5 illustrates a loading operation for processing the \*\*\*.mat file. In other words, the \*\*\*.mat file is open to load stored variables.

Figure 6:
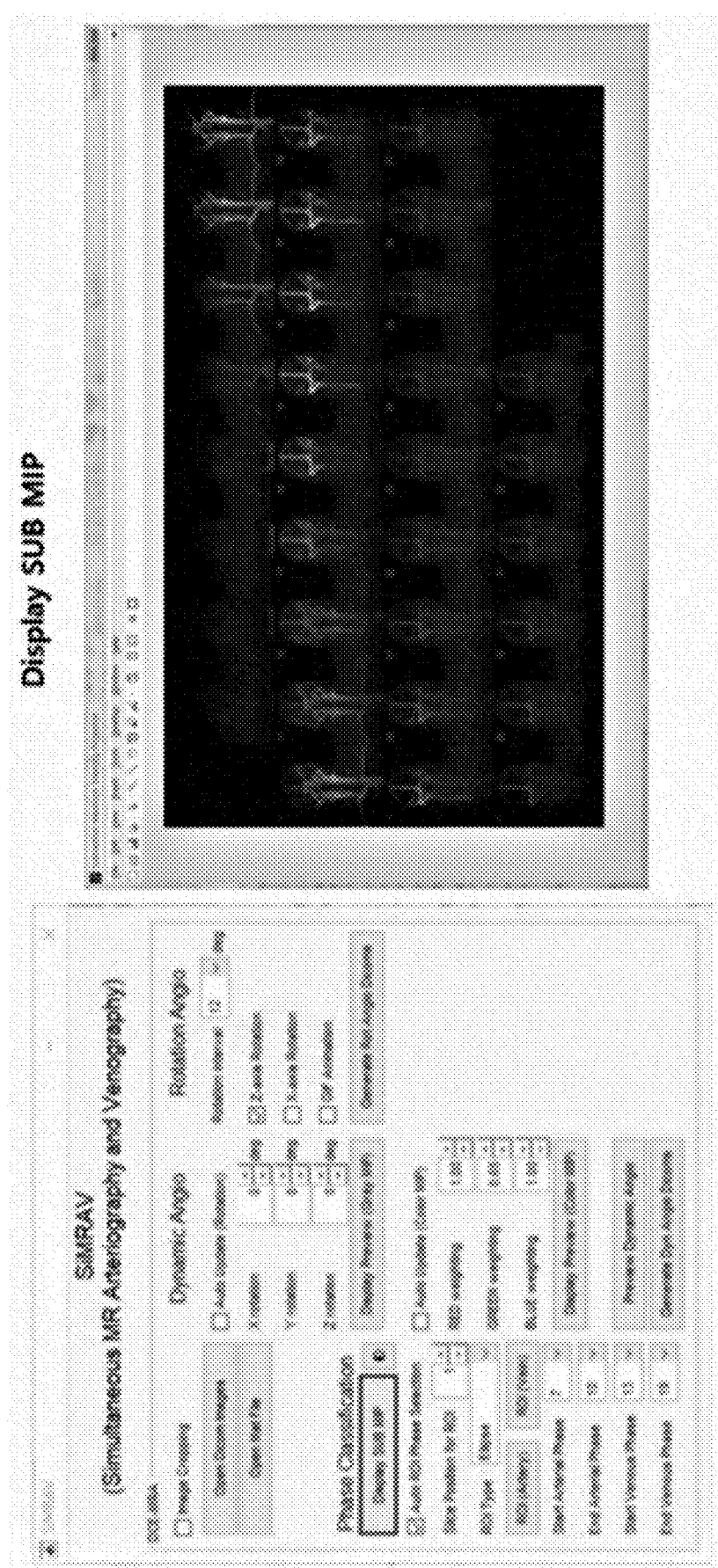

FIG. 6 illustrates a process of processing the \*\*\*.mat file and displaying subtraction MIP (SUB MIP in FIG. 6) images arranged according to phases. In this process, it may be checked whether an omitted or damaged phase exists and whether the order is well organized.

Figure 7:
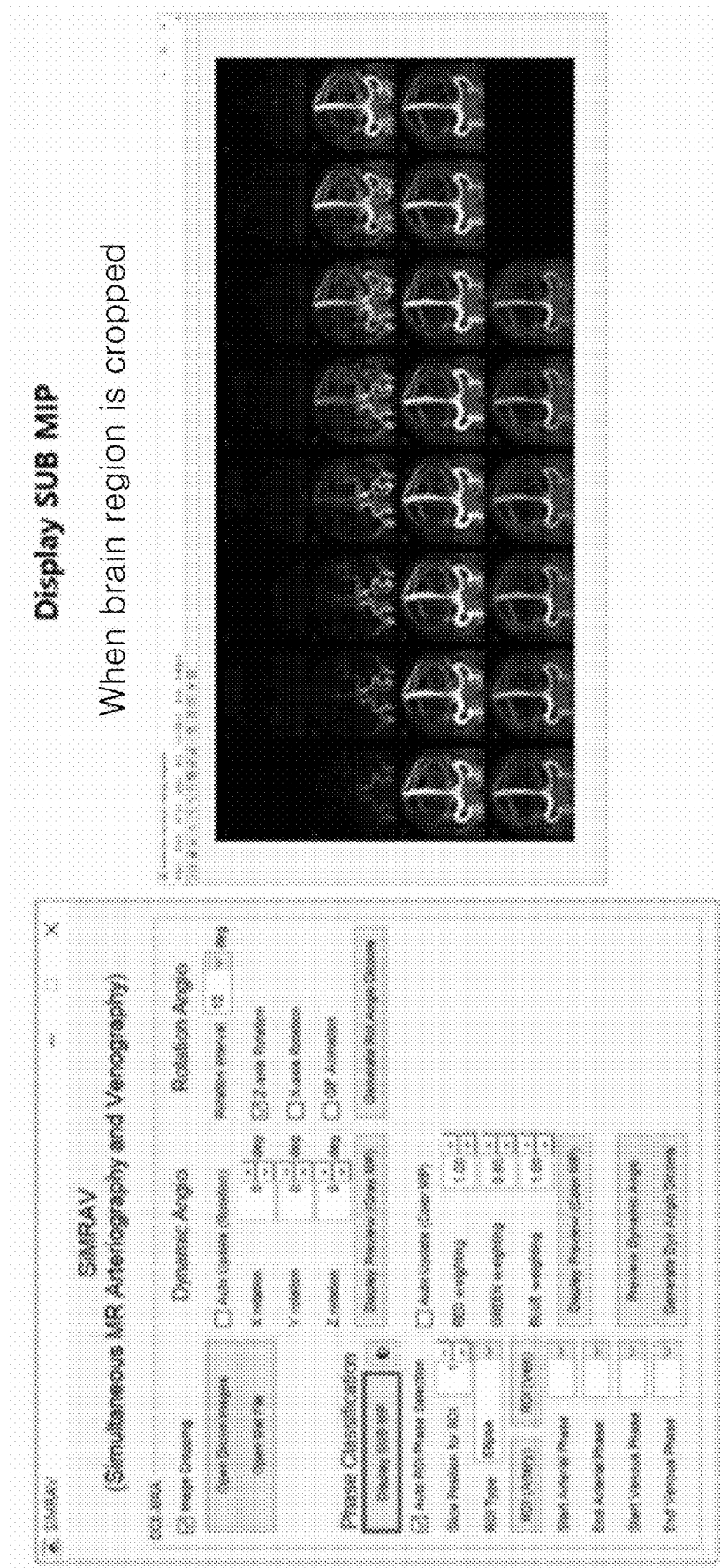

FIG. 7 illustrates display of a subtraction MIP image when the brain region is cropped.

Figure 8:
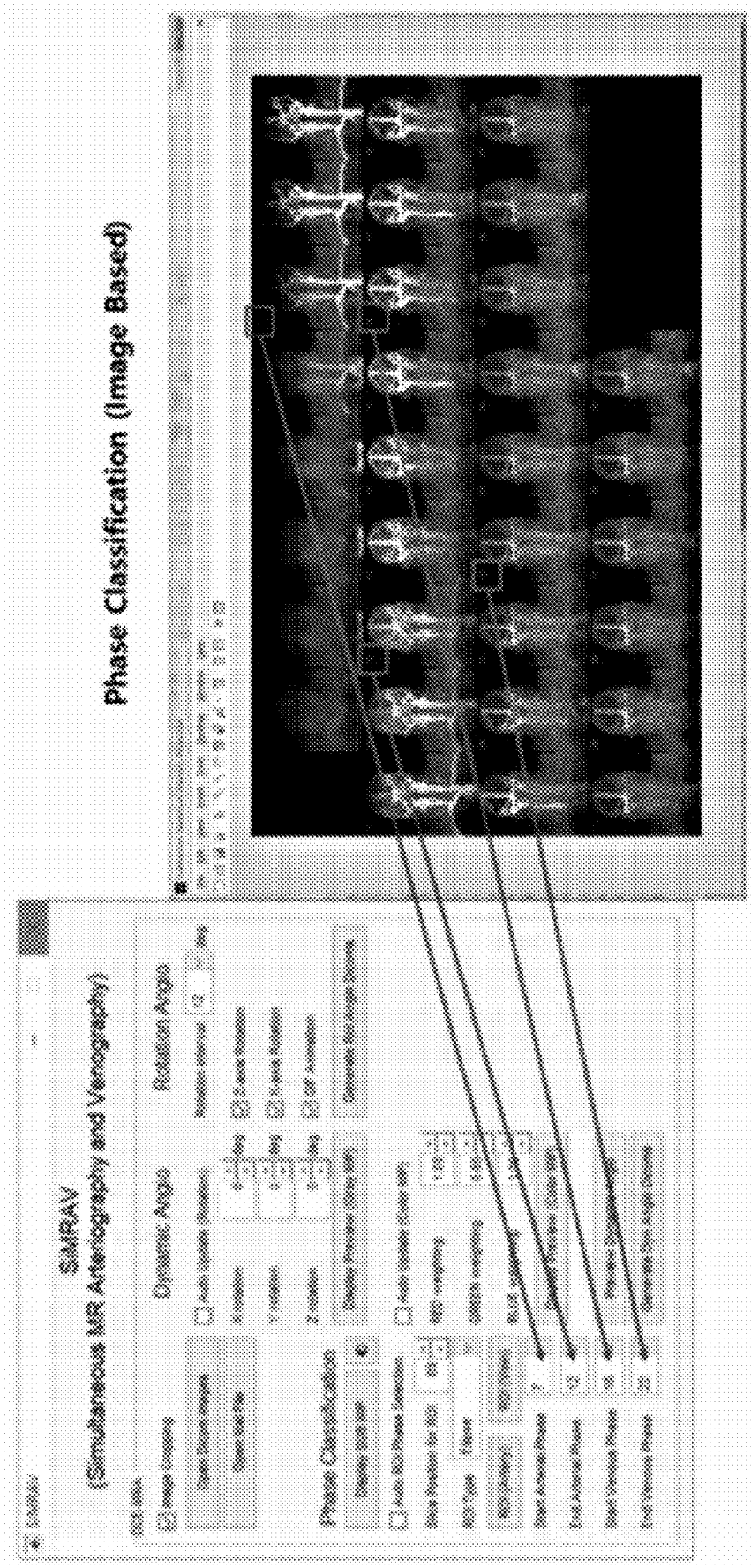
FIGS. 8 and 9 illustrate a process of manually designating phases in banks while watching only a subtraction MIP image or making time-intensity curves by setting regions of interest (ROIs) on the cerebral artery and cerebral vein and then classifying an arterial phase, a capillary phase, and a venous phase, and then preparing for subtraction and color coding based on the three phases.

FIG. 8 illustrates a method of determining a phase such as the arterial phase, the capillary phase, or the venous phase through manual designation while watching the subtraction MIP image. Each phase may be determined by writing an appropriate phase number in the left blank space, based on the signal intensities of visible arteries and veins.

Figure 9:
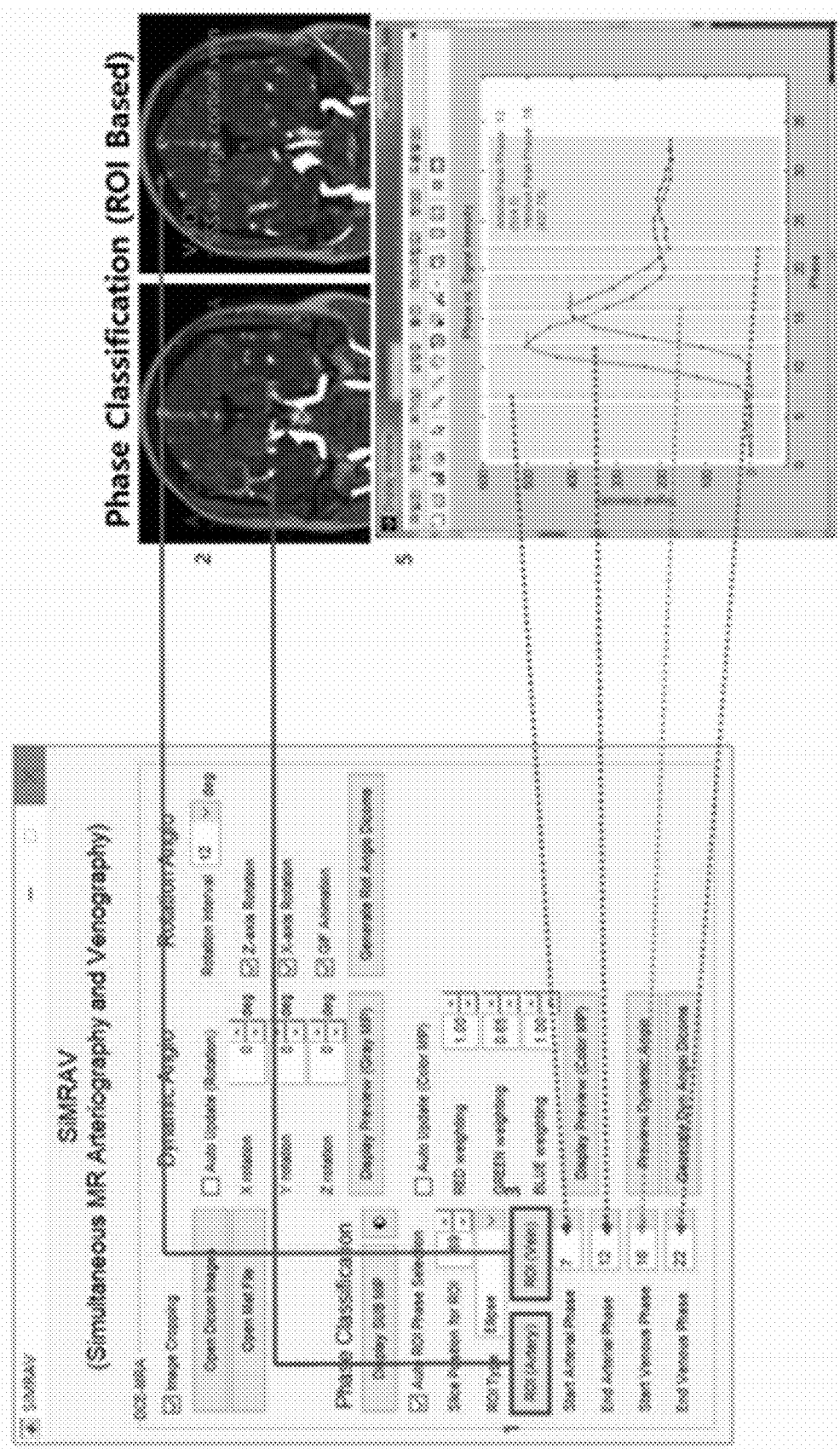

FIG. 9 illustrates that phases are automatically determined when ROIs are designated on the M1 segment of the MCA and the SSS on a coronal angiography image window newly opened by clicking an ROI (artery) window and an ROI (vein) window and time-intensity curves of the artery and vein are created. The method of FIG. 9 is a method of more clearly and more objectively determining a phase. When there is an abnormality in blood flow due to occlusion or stenosis of one artery, a normal blood vessel is designated as much as possible.

Figure 10:
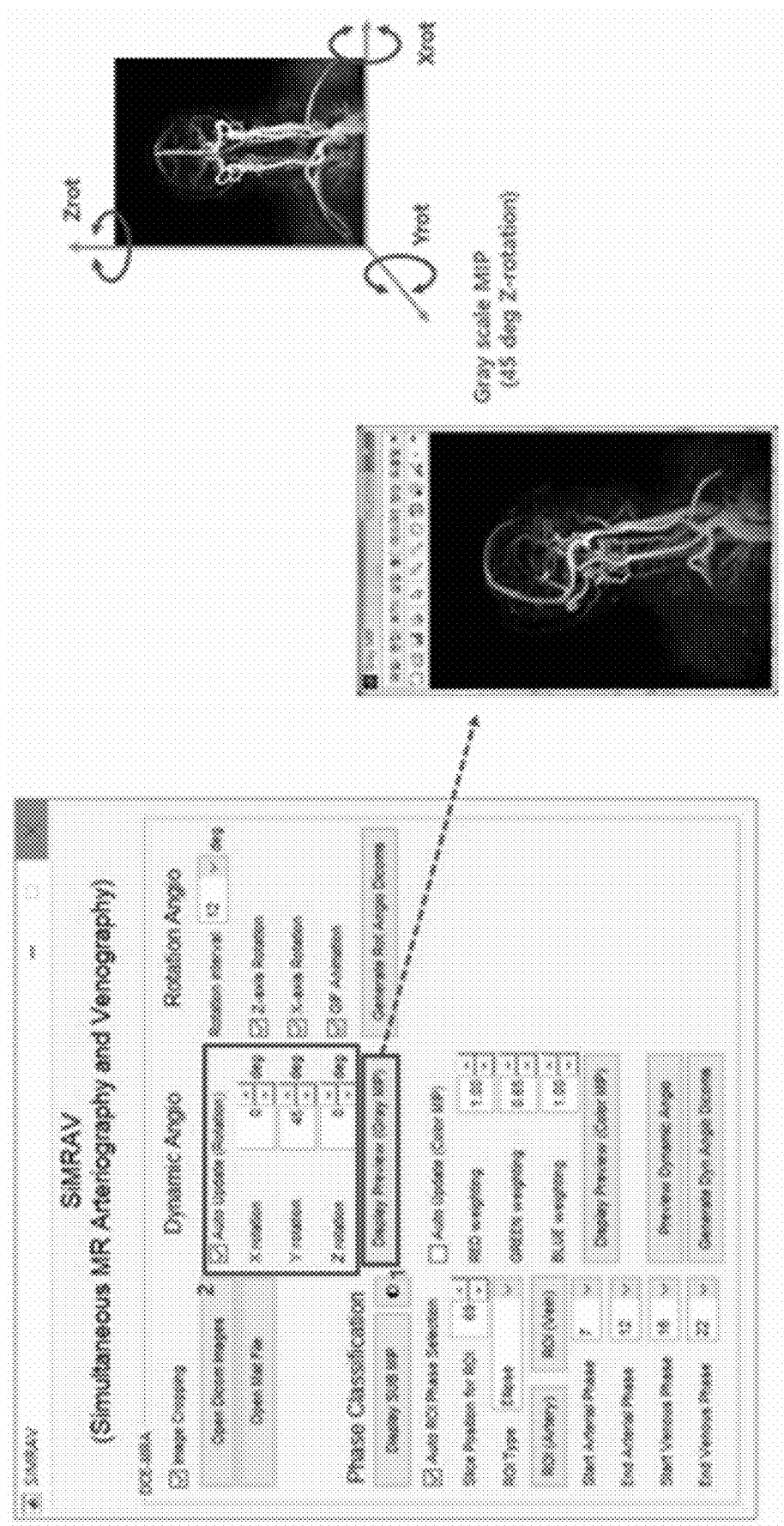
FIG. 10 illustrates a process of obtaining a desired projection by freely rotating about x, y, and z axes.

FIG. 10 illustrates a process of obtaining a projection in which a desired lesion or a specific blood vessel is well visible by freely rotating about the x, y, and z axes. First, an MR angiography image may be rotated by displaying grayscale MR angiography in which signals of all phases are summed, as an MIP image (gray MAIP image of FIG. 10), as indicated by reference number 1, and directly designating rotation angles about the x, y, and z axes in order to obtain a desired projection. When auto update (rotation) is checked, every time rotation is changed about the x, y, and z axes, display is immediately updated. X, y, and z axis rotations minutely change by 1 degree at a time. Thus, in order to give a large angle change, Auto Update is unchecked and a desired angle is input, and then Display Preview (Gray MIP) is clicked, as indicated by reference numeral 1. Then, a rotation by a large angle may be made at once.

Figure 11:
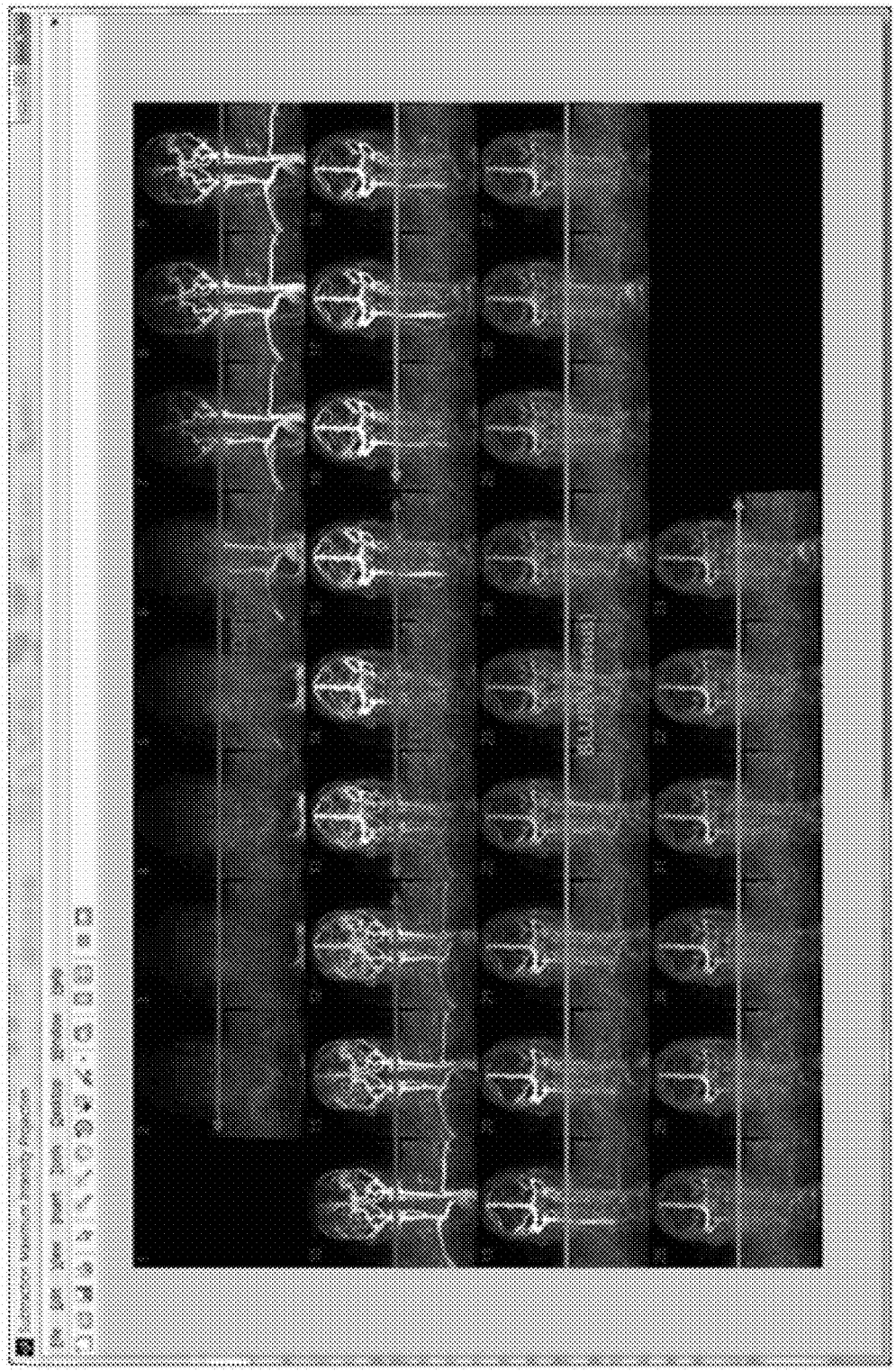
FIG. 11 illustrates color coding according to phases in an image information post-processing process of 4D MR angiography according to the present disclosure.

FIG. 11 illustrates a process of coding arterial phase blood vessels, capillary phase blood vessels, and venous phase blood vessels of grayscale 4D MR angiography determined based on time-intensity curves of the artery and vein in red, green, and blue colors.

In addition, in order to express a wash-in/wash-out (blood flow fills in and out) phenomenon of blood vessels in color-coded 4D MR angiography, time-intensity curve information of the artery and vein may be converted into a color-weighting conversion factor, and the color-weighting conversion factor may be additionally applied to changes in the colors of arteries (red) and veins (blue) to realize a color 4D MR angiography image in which dynamic changes in blood flow over time have been reflected, and color weightings of red, blue, and green may be manually adjusted so that blood vessels at a desired time, such as arteries or veins, are more visible.

A method of realizing color 3D subtraction MR arteriography and color 3D subtraction MR venography through image information post-processing of 4D MR angiography, according to an embodiment of the present disclosure, is as follows.

First, a mask is created to reconstruct grayscale 3D subtraction MR arteriography and grayscale 3D subtraction MR venography before color coding, and the mask is created using the equation below.

Arterial Mask(3D Volume)={Arterial Phase(3D Volume)−Venous Phase(3D Volume)}>0

Venous Mask(3D Volume)={Venous Phase(3D Volume)−Arterial Phase(3D Volume)}>0  <Mask Generation>

The arterial mask is created so that a pixel greater than 0 has a value of 1 and the remaining pixels have a value of 0, by subtracting the 3D volume of a venous phase from the 3D volume of an arterial phase on a pixel-by-pixel basis. The venous mask is created so that a pixel greater than 0 has a value of 1 and the remaining pixels have a value of 0, by subtracting the 3D volume of the arterial phase from the 3D volume of the venous phase on a pixel-by-pixel basis.

Grayscale 3D subtraction MR arteriography is generated by multiplying the 3D volume of the created arterial mask by the 3D volume of the arterial phase for each pixel to remove unnecessary portions other than information of arteries, and then performing an MIP process, and uses the equation below.

Grayscale 3D subtraction MR venography is generated by multiplying the 3D volume of the created venous mask by the 3D volume of the venous phase for each pixel to remove unnecessary portions other than information of veins, and then performing an MIP process, and uses the equation below.

Subtraction MR arteriography=MIP{Arterial Phase (3D Volume)\*Arterial Mask(3D Volume)}

Subtraction MR venography=MIP{Venous Phase(3D Volume)\*
Venous Mask(3D Volume)}   <Generation of Subtraction-Arteriography and Subtraction-Venography>

When grayscale 3D subtraction MR arteriography and grayscale subtraction MR venography created through the above process are multiplied by color weighting factors, color 3D subtraction MR arteriography and color 3D subtraction MR venography may be generated.

Figure 12:
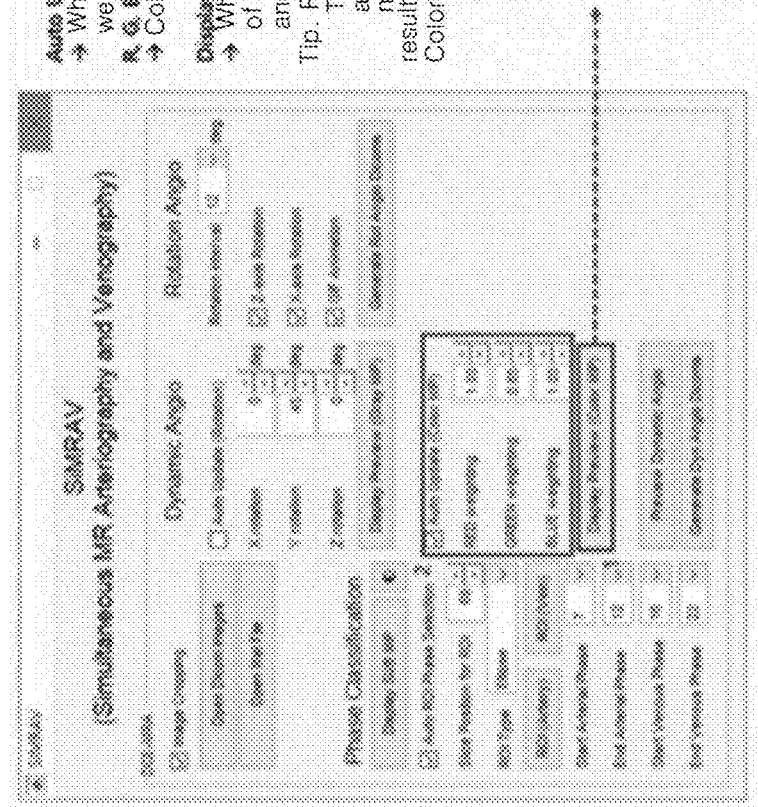
FIG. 12 illustrates a method of setting an appropriate weighting value for color coding in an image information post-processing process of 4D MR angiography according to the present disclosure.

FIG. 12 illustrates a process of displaying color 3D MR angiography, color 3D subtraction MR arteriography, and color 3D subtraction MR venography, and shows that the color weightings of red, blue, and green may be manually adjusted so that blood vessels of a desired phase (such as artery and vein images) and hemodynamic change are more clearly visible.

Figure 13:
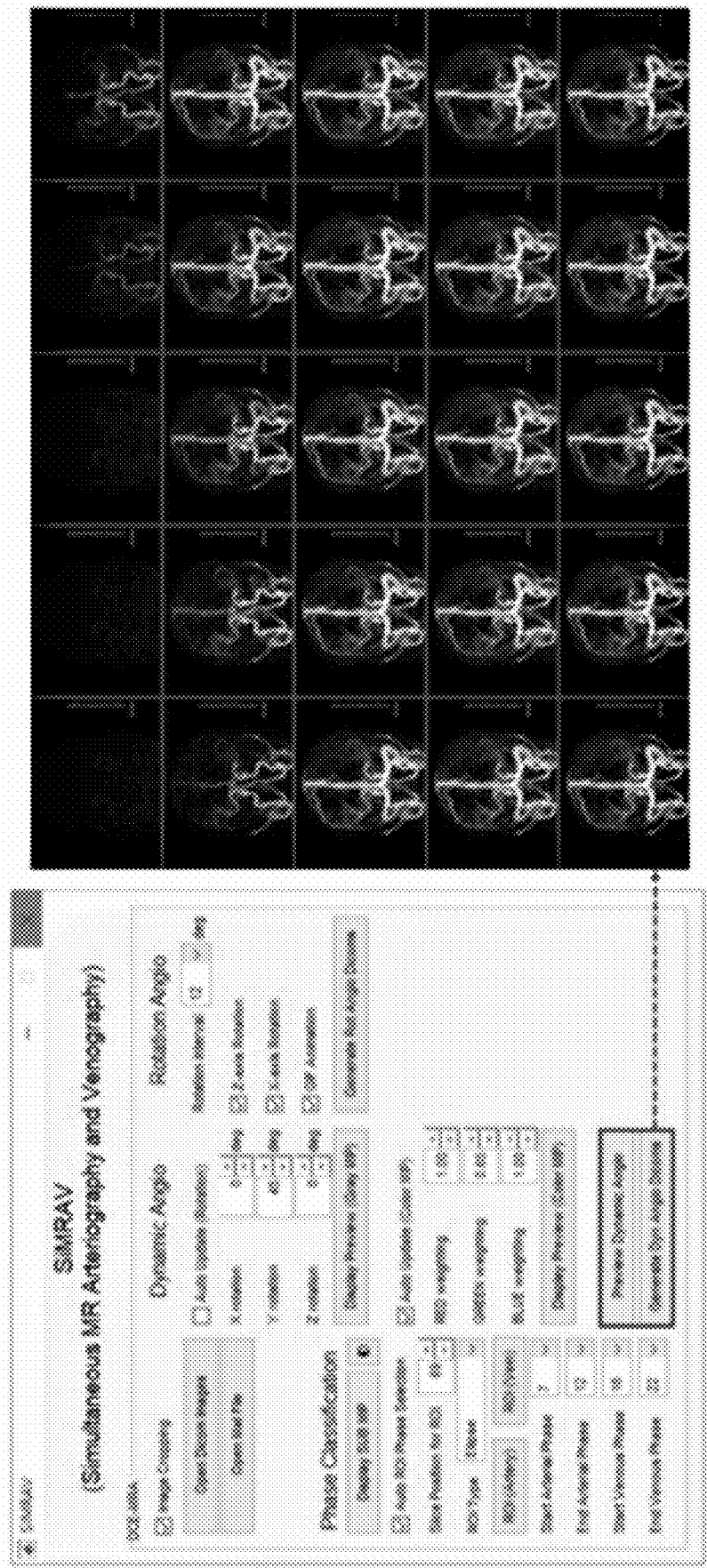
FIG. 13 illustrates a process of outputting, previewing, and storing color-coded 4D MR angiography.

FIG. 13 illustrates a process of outputting, previewing, and storing color-coded 4D MR angiography. In this process, color-coded 4D MR angiography and grayscale 4D MR angiography are simultaneously stored in a Dicom format and a moving picture (GIF) format, and color-coded 3D MR angiography in which all phases are incorporated is also stored.

Figure 14:
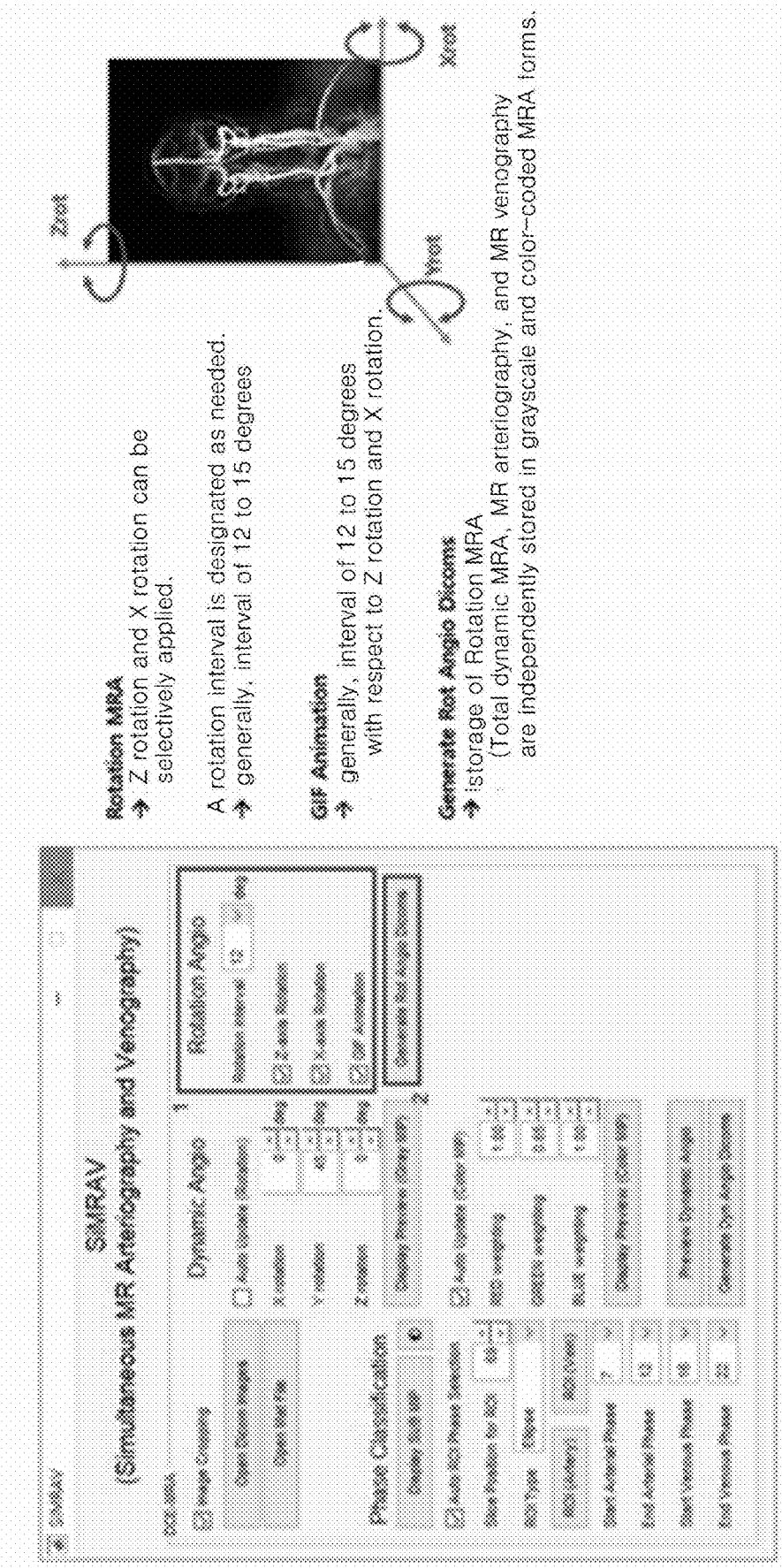
FIG. 14 illustrates a rotator that rotates an image along a desired axis and by a desired angle in a program implementing an image information post-processing method of 4D MR angiography according to the present disclosure.

FIG. 14 illustrates a rotator that rotates the grayscale and color 3D MR angiography, the grayscale and color 3D subtraction MR arteriography, and the grayscale and color 3D subtraction MR venography images obtained through the aforementioned processes by desired angles and displaying a result of the rotations. Images rotated around the z-axis and x-axis, respectively, are stored in the Dicom format and the moving picture (GIF) format. Referring to FIG. 14, z-axis rotation and x-axis rotation may be selectively applied to obtained MR blood vessel images, and a rotation interval (generally an interval of 10 to 30 degrees) may be designated as needed. Moreover, images that rotate about the z-axis and the x-axis may be created as GIF animations.

Figure 15A:
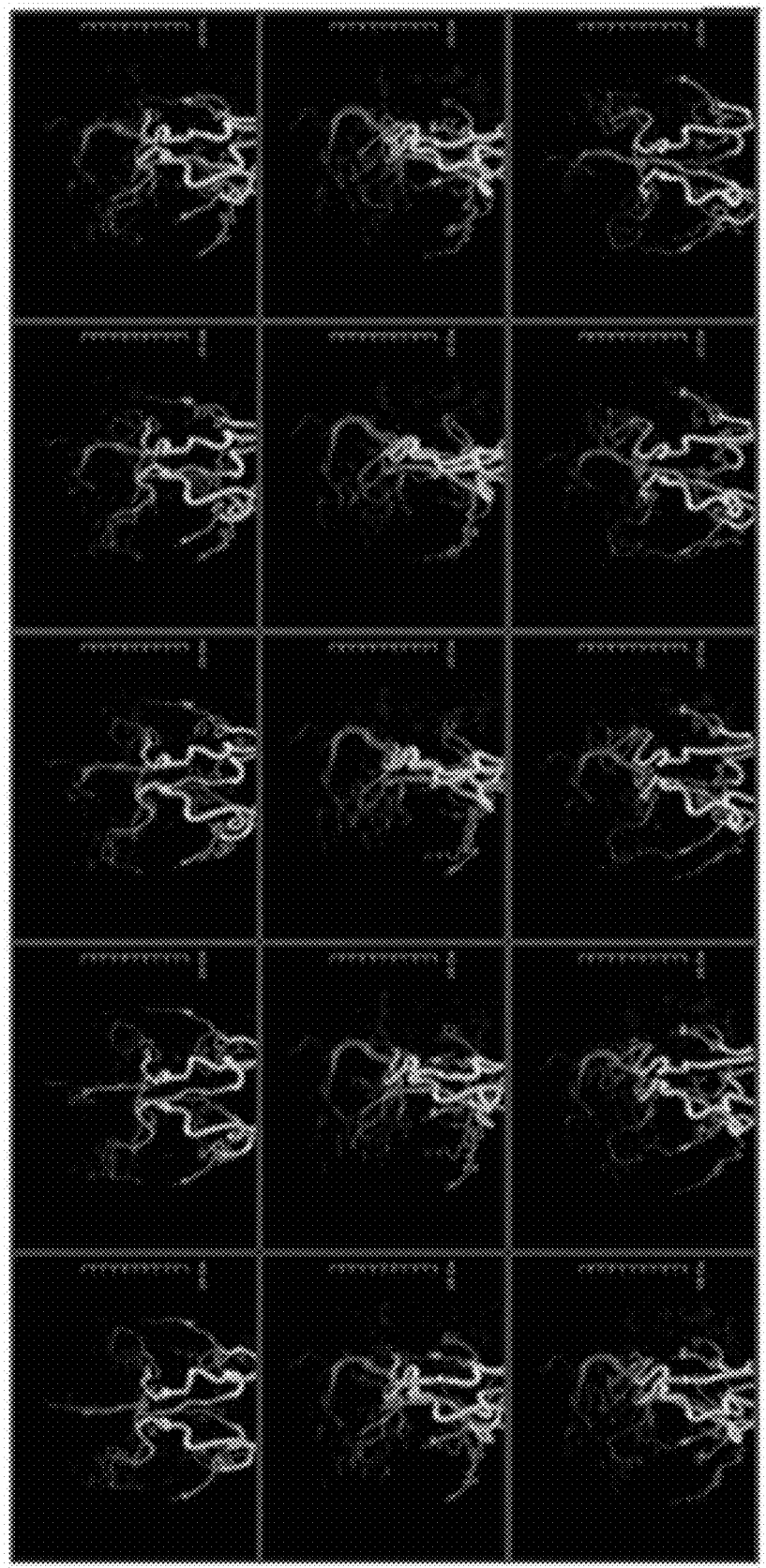
FIG. 15A is an image in which grayscale 3D subtraction MR arteriography images obtained by selecting only a brain part and then rotating horizontally the brain part about the z axis are sequentially arranged according to rotation angles.
Figure 15B:
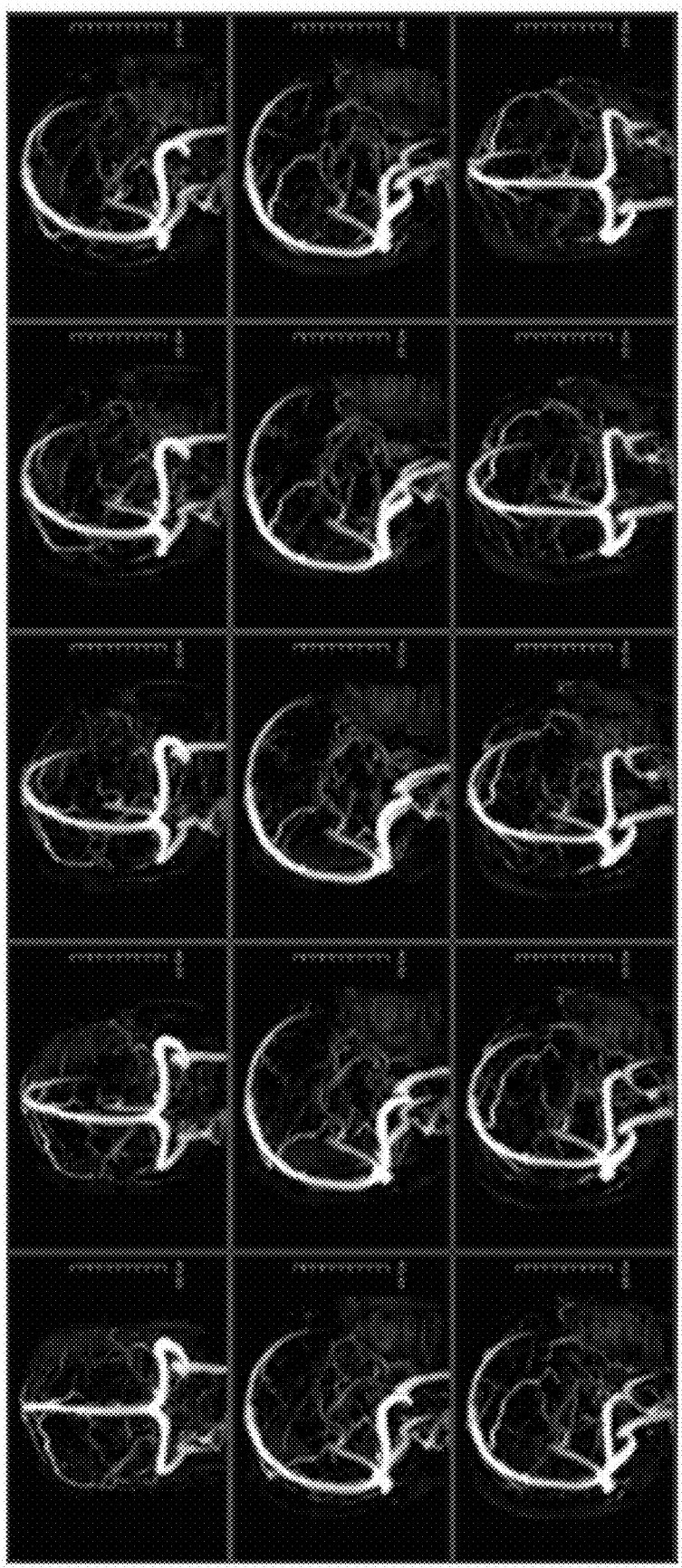
FIG. 15B is an image in which grayscale 3D subtraction MR venography images obtained by selecting only a brain part and then rotating horizontally the brain part about the z axis are sequentially arranged according to rotation angles.
Figure 16A:
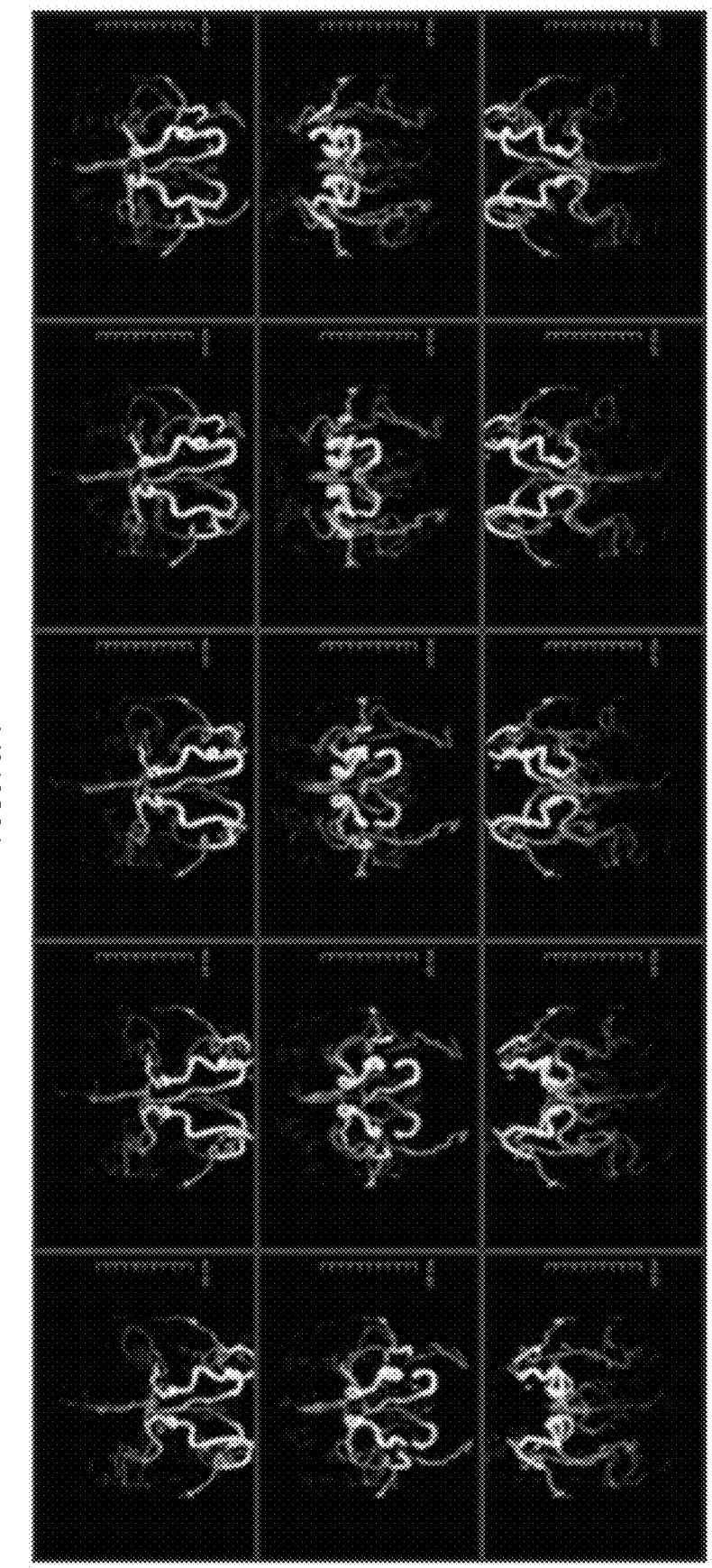
FIG. 16A is an image in which grayscale 3D subtraction MR arteriography images obtained by selecting only a brain part and then rotating vertically the brain part about the x axis are sequentially arranged according to rotation angles.
Figure 16B:
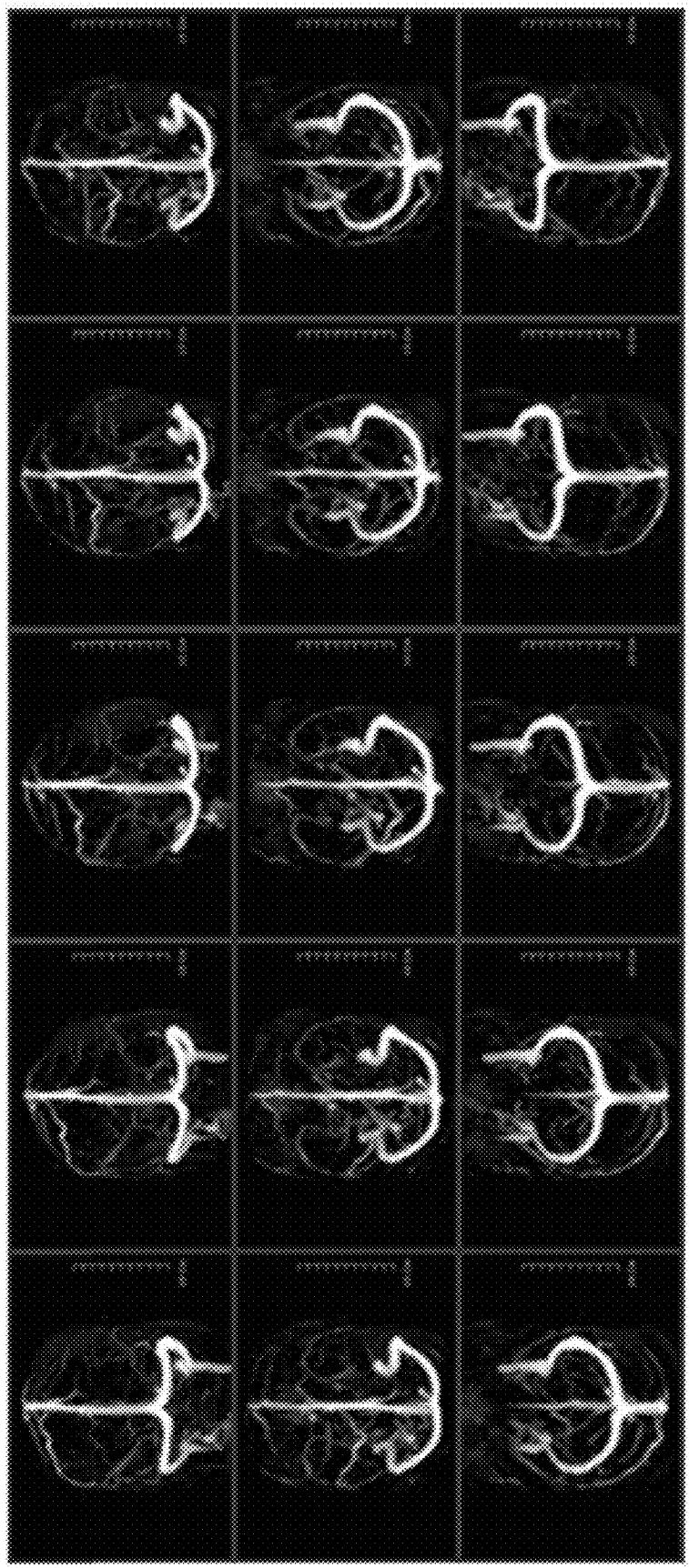
FIG. 16B is an image in which grayscale 3D subtraction MR venography images obtained by selecting only a brain part and then rotating vertically the brain part about the x axis are sequentially arranged according to rotation angles.

FIG. 15A is an image in which grayscale 3D subtraction MR arteriography images obtained by selecting only a brain part and then rotating horizontally the brain part about the z axis are sequentially arranged according to rotation angles. FIG. 15B is an image in which grayscale 3D subtraction MR venography images obtained by selecting only a brain part and then rotating horizontally the brain part about the z axis are sequentially arranged according to rotation angles. FIG. 16A is an image in which grayscale 3D subtraction MR arteriography images obtained by selecting only a brain part and then rotating vertically the brain part about the x axis are sequentially arranged according to rotation angles. FIG. 16B is an image in which grayscale 3D subtraction MR venography images obtained by selecting only a brain part and then rotating vertically the brain part about the x axis are sequentially arranged according to rotation angles.

Figure 17A:
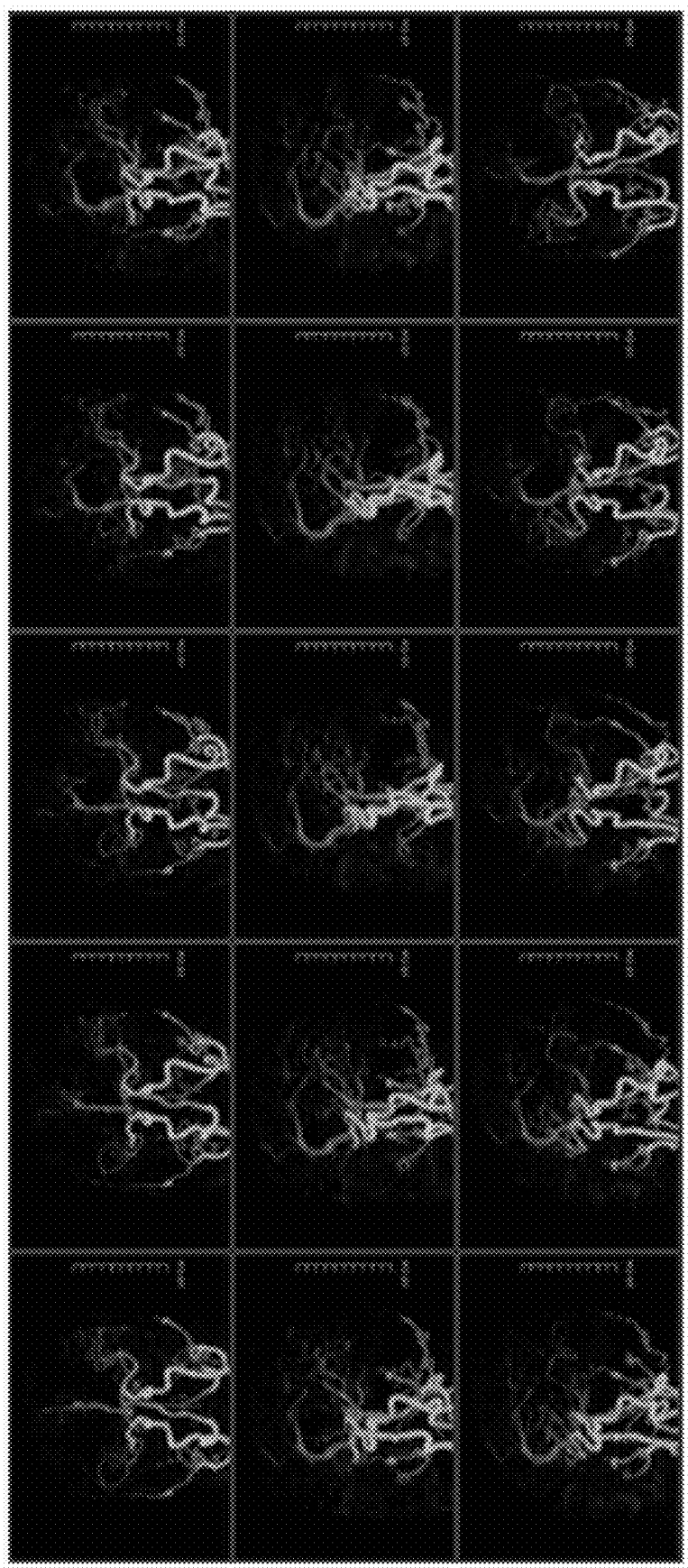
FIG. 17A is an image in which color 3D subtraction MR arteriography images obtained by selecting only a brain part and then rotating horizontally the brain part about the z axis are sequentially arranged according to rotation angles.
Figure 17B:
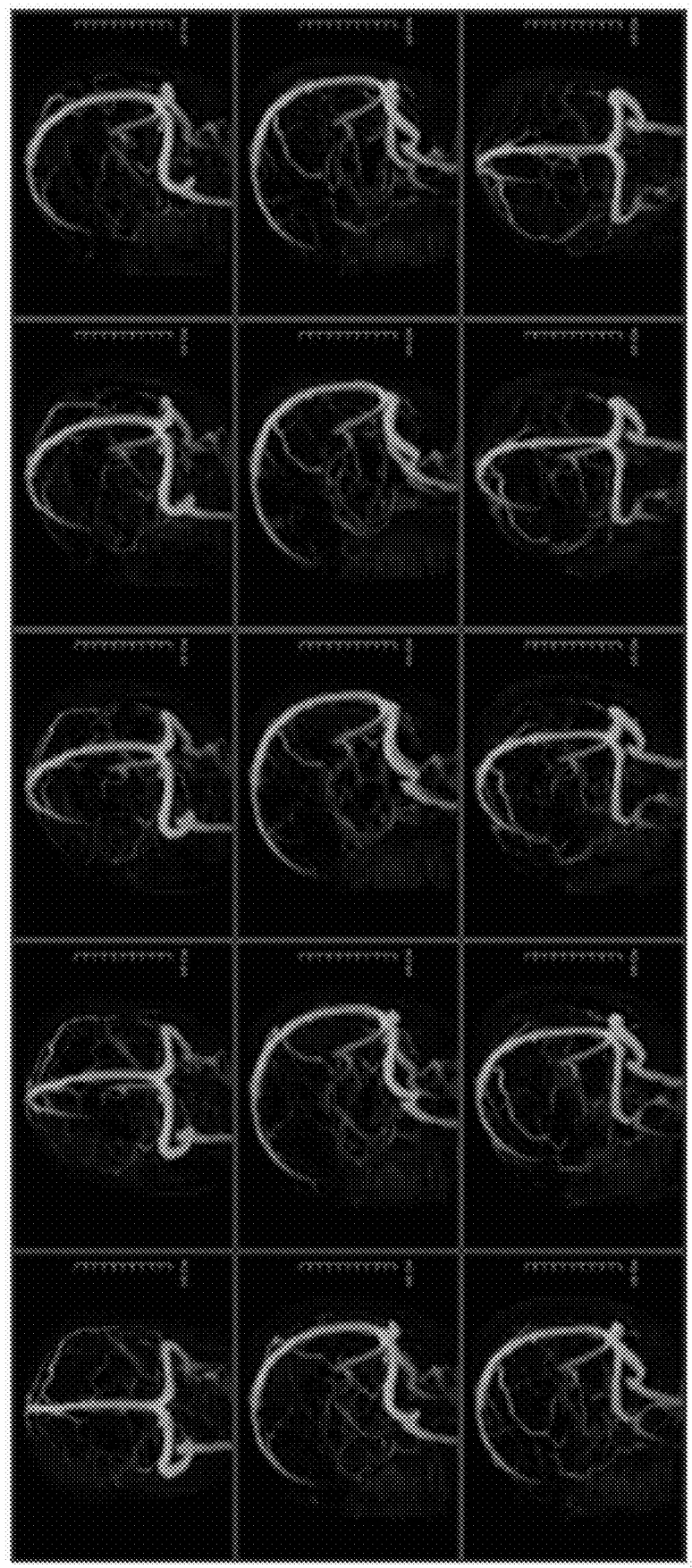
FIG. 17B is an image in which color 3D subtraction MR venography images obtained by selecting only a brain part and then rotating horizontally the brain part about the z axis are sequentially arranged according to rotation angles.
Figure 17C:
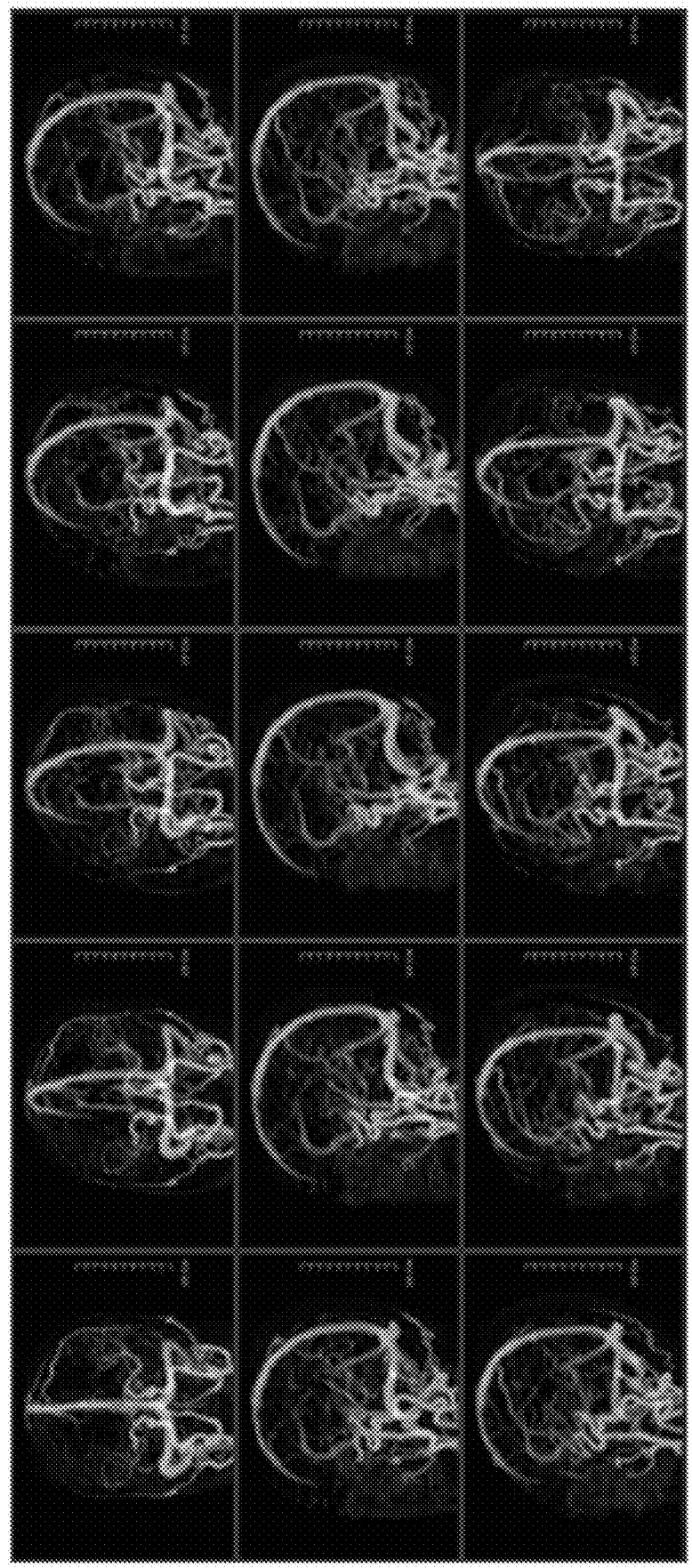
FIG. 17C is an image in which color-coded 3D subtraction MR angiography images obtained by selecting only a brain part and then rotating horizontally the brain part about the z axis are sequentially arranged according to rotation angles.
Figure 18A:
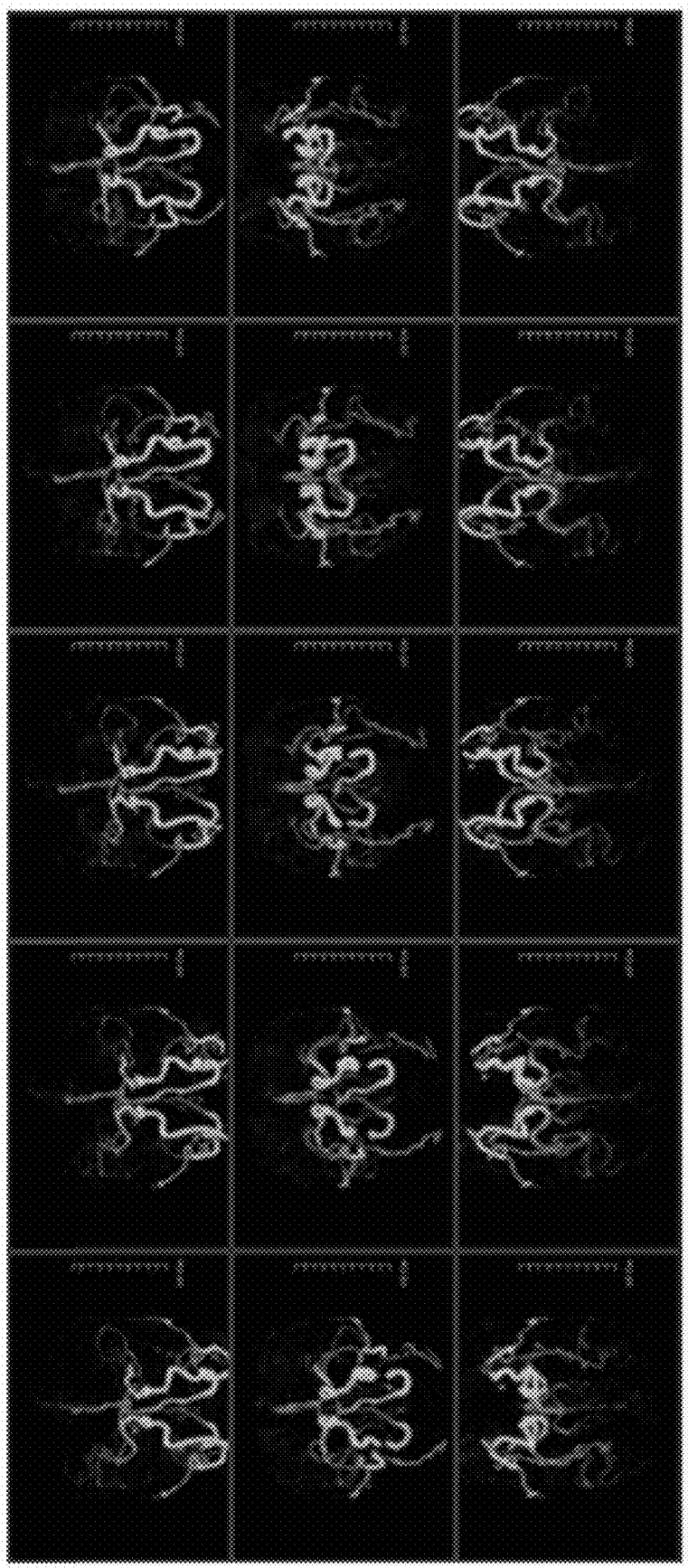
FIG. 18A is an image in which color 3D subtraction MR arteriography images obtained by selecting only a brain part and then rotating vertically the brain part about the x axis are sequentially arranged according to rotation angles.
Figure 18B:
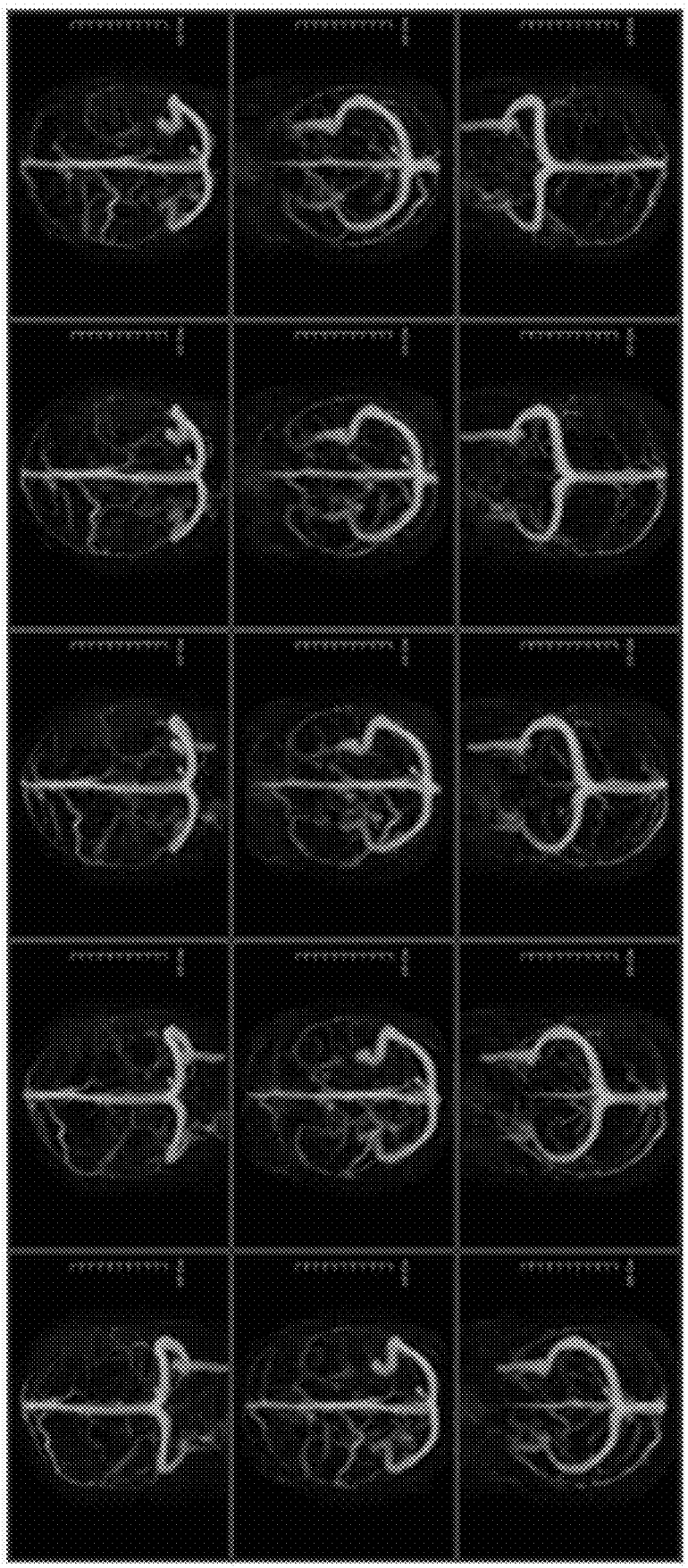
FIG. 18B is an image in which color 3D subtraction MR venography images obtained by selecting only a brain part and then rotating vertically the brain part about the x axis are sequentially arranged according to rotation angles.
Figure 18C:
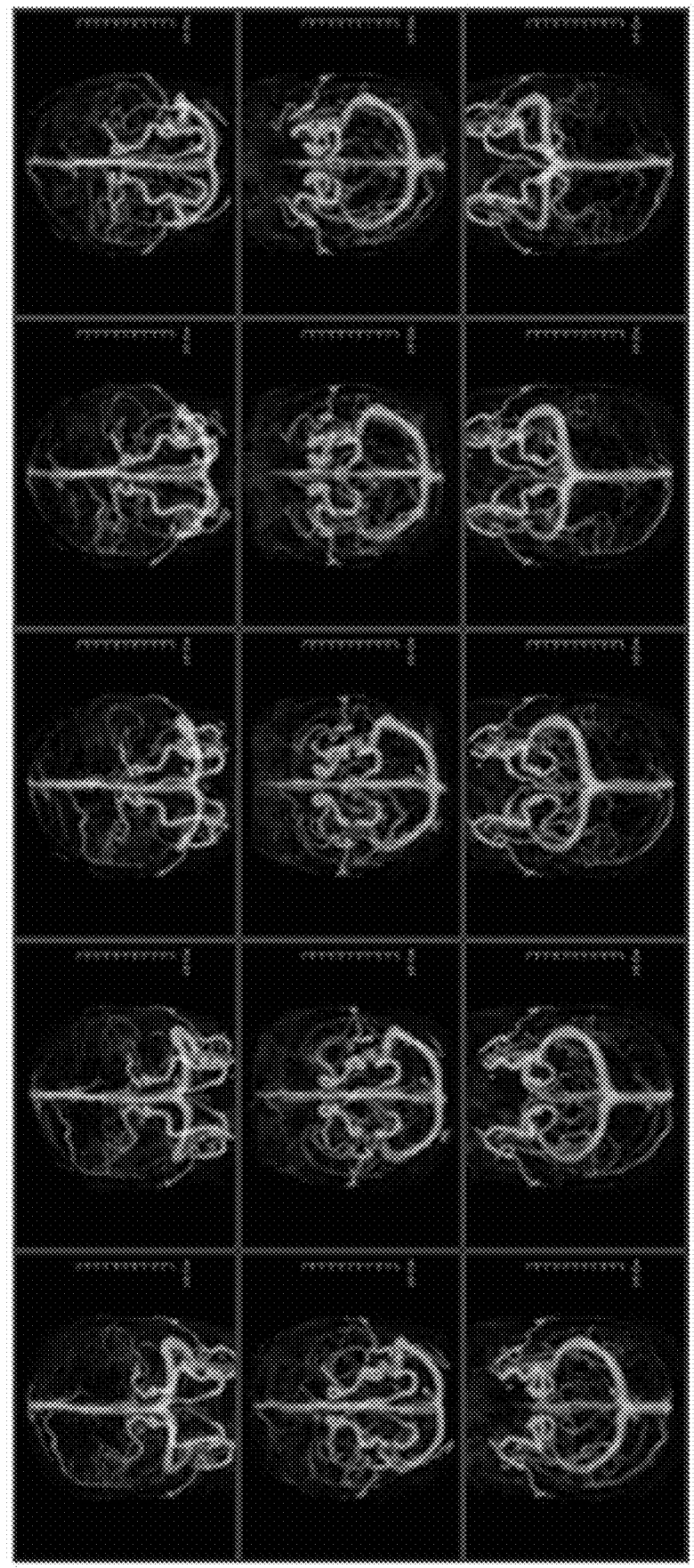
FIG. 18C is an image in which color-coded 3D subtraction MR angiography images obtained by selecting only a brain part and then rotating vertically the brain part about the x axis are sequentially arranged according to rotation angles.
Figure 19:
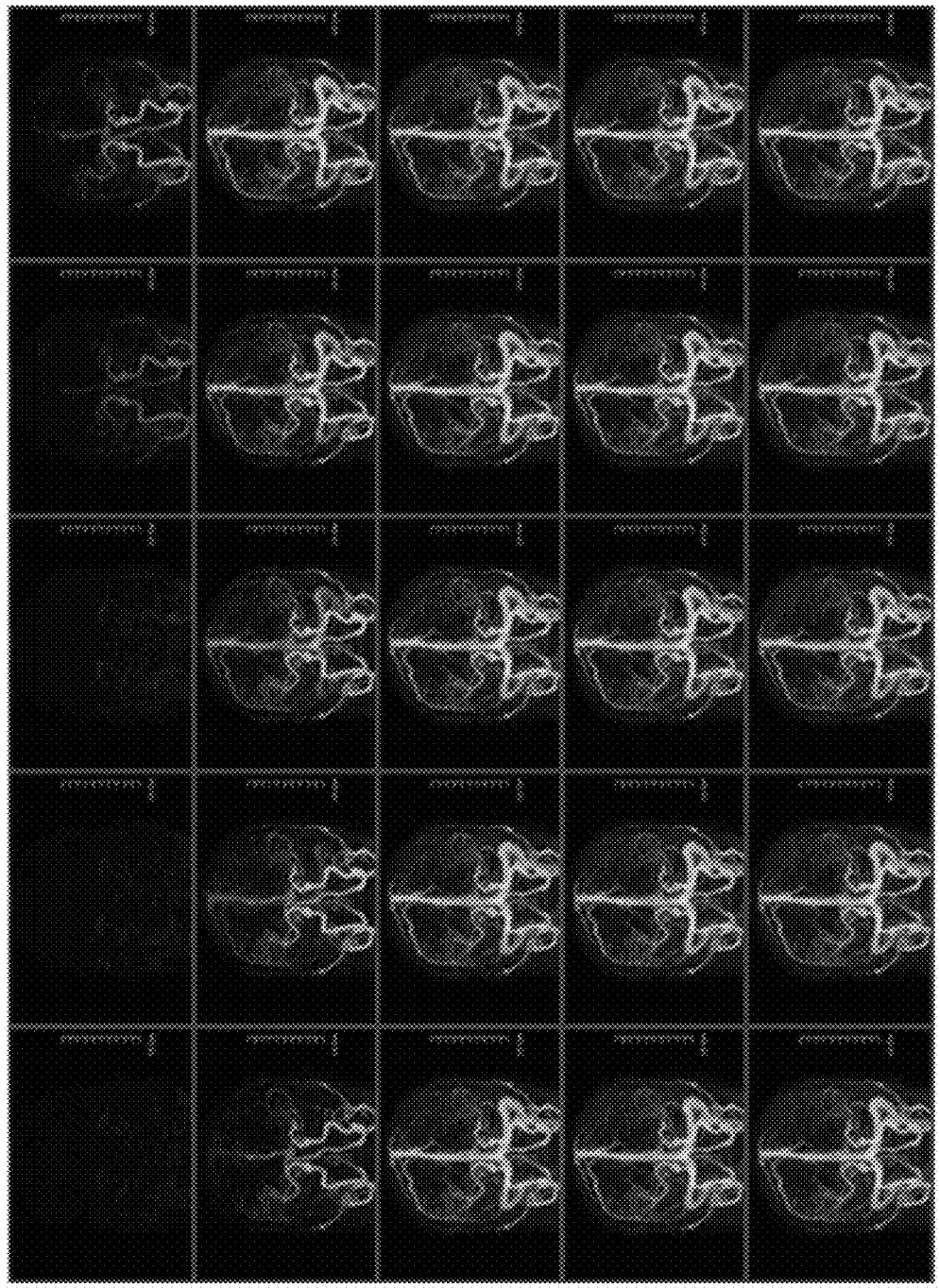
FIG. 19 is an arrangement of color-coded 4D MR angiography images obtained by selecting only a brain part, in a time order.

FIG. 17A is an image in which color 3D subtraction MR arteriography images obtained by selecting only a brain part and then rotating horizontally the brain part about the z axis are sequentially arranged according to rotation angles. FIG. 17B is an image in which color 3D subtraction MR venography images obtained by selecting only a brain part and then rotating horizontally the brain part about the z axis are sequentially arranged according to rotation angles. FIG. 17C is an image in which 3D color-coded subtraction MR angiography images obtained by selecting only a brain part and then rotating horizontally the brain part about the z axis are sequentially arranged according to rotation angles. FIG. 18A is an image in which color 3D subtraction MR arteriography images obtained by selecting only a brain part and then rotating vertically the brain part about the x axis are sequentially arranged according to rotation angles. FIG. 18B is an image in which color 3D subtraction MR arteriography images obtained by selecting only a brain part and then rotating vertically the brain part about the x axis are sequentially arranged according to rotation angles. FIG. 18C is an image in which 3D color-coded subtraction MR angiography images obtained by selecting only a brain part and then rotating vertically the brain part about the x axis are sequentially arranged according to rotation angles. FIG. 19 is an arrangement of color-coded 4D MR angiography images of only a brain part in a time order.

The present disclosure may be embodied as computer-readable codes (computer including all devices having an information processing function) on a computer-readable recording medium. The computer-readable recording medium is any type of recording device that stores data which can thereafter be read by a computer system. Examples of the computer-readable recording device include ROM, RAM, CD-ROMs, magnetic tapes, floppy discs, and optical data storage media. A term "unit" used herein may be a hardware component such as a processor or circuit, and/or a software component executed by a hardware component such as a processor.

Although the present disclosure has been described with reference to the embodiments shown in the drawings, this is merely an example. It will be understood by one of ordinary skill in the art that various modifications and equivalent other embodiments may be made without departing from the spirit and scope as defined by the following claims.

What is claimed is:

1. A simultaneous implementation method of three-dimensional (3D) subtraction magnetic resonance (MR) arteriography, 3D subtraction MR venography, and color-coded four-dimensional (4D) MR angiography through post-processing of image information of 4D MR angiography, the simultaneous implementation method comprising:

a first operation of, when a time unit for generating and processing a 4D MR angiography image is a phase, loading 4D MR angiography image data obtained repeatedly from the aortic arch to the top of the head for each phase, extracting an entire region or a necessary region, and storing the extracted region as a file having entire image information including time, space, and signal intensity information;

a second operation of opening the stored file to output subtraction maximum intensity projection (MIP) images arranged in a time order, and checking whether 4D MR angiography images are arranged in a time order;

a third operation of generating time-intensity curves of the artery and vein that change according to the concentration and flow of a contrast medium, by designating regions of interest (ROIs) on the M1 segment of the middle cerebral artery and the superior sagittal sinus, and determining an arterial phase, a capillary phase, and a venous phase;

a fourth operation of color-coding all blood vessels in different colors according to phases when the blood vessels are seen, after processes of dividing blood vessel image information according to the arterial phase, the capillary phase, and the venous phase, extracting only an artery signal by subtracting venous phase image information from arterial phase image information, and extracting only a vein signal by subtracting arterial phase image information from venous phase image information; and a fifth operation of storing and outputting image information of 3D subtraction MR arteriography and 3D subtraction MR venography generated in the fourth operation as a grayscale and a color scale, and storing and outputting a color-coded 4D MR angiography image, in which entire hemodynamic information of a 4D MR angiography image is emphasized, and a color-coded 3D MR angiography image.

2. The simultaneous implementation method of claim 1, wherein the first operation further comprises an operation of opening a cropping window to remove unnecessary portions from the entire field of view, designating only a desired region, and storing an angiographic image file of a specific region, in order to obtain an angiographic image of the specific region.

3. The simultaneous implementation method of claim 1, wherein the fourth operation comprises a color coding method of allowing arterial phase blood vessels from a time point when an artery signal starts to rise to the arterial peak phase when the arterial signal intensity is greatest to be displayed in red, allowing venous phase blood vessels from the venous peak phase when the venous signal intensity is greatest to a time point when the venous signal decreases to a plateau to be displayed in blue, and allowing blood vessels between the arterial peak phase and the venous peak phase to be displayed in green, based on time-intensity curves of the artery and vein, and comprises additionally adjusting color weightings of red, blue, and green in order to make blood vessels of a desired phase and hemodynamic change more visible.

4. The simultaneous implementation method of claim 1, wherein an arterial mask only having a value greater than or equal to 0 is created by subtracting venous phase signals from arterial phase signals, and then subtraction MR arteriography is generated by updating an arterial phase MIP by multiplying the arterial phase MIP by the arterial mask, and a venous mask only having a value greater than or equal to 0 is created by subtracting arterial phase signals from venous phase signals, and then subtraction MR venography is generated by updating a venous phase MIP by multiplying the venous phase MIP by the venous mask.

5. The simultaneous implementation method of claim 1, further comprising:
to obtain a projection in which a lesion or a specific blood vessel is well visible, by designating various angles around x, y, and z axes, rotating an image, and checking and processing an updated display; and
obtaining and storing continuous images rotated at a certain angle designated by a user, based on the x axis or the z axis.

6. A medical imaging system for simultaneously implementing three- dimensional (3D) subtraction magnetic resonance (MR) arteriography, 3D subtraction MR venography, and color-coded four-dimensional (4D) MR angiography through post-processing of image information of 4D MR angiography, the medical imaging system comprising:
an input interface configured to receive, as an input, 4D MR angiography image data obtained repeatedly from the aortic arch to the top of the head at intervals of a predetermined time;
an extractor configured to cut out an entire portion or a desired portion from the 4D MR angiography image data, and store the cut-out portion as a file including both information about the shape and location of blood vessels and information about changes in blood flow and signal intensity according to time;
a phase setter configured to output the 4D MR angiography image as subtraction maximum intensity projection (MIP) images arranged in a time order, designate regions of interest (ROIs) on the M1 segment of the middle cerebral artery (MCA) and the superior sagittal sinus (SSS), based on the subtraction MIP images to create a time-intensity curves of the cerebral artery and cerebral vein, and then classify an arterial phase, a capillary phase, and a venous phase;
a subtraction image processor configured to generate a subtraction MR arteriography image and a subtraction MR venography image by distinguishing and calculating blood vessels from a time point when the arterial signal starts to rise to the arterial peak phase when the arterial signal intensity is greatest, blood vessels from the venous peak phase when the venous signal intensity is greatest to a time point when the venous signal decreases to a plateau, and blood vessel image information between the arterial peak phase and the venous peak phase;
a color coding unit configured to classify blood vessels of a 3D subtraction MR arteriography image, a 3D subtraction MR venography image, and a 4D MR angiography image into arteries, capillaries, and veins according to phases when the blood vessels are seen, and distinguish the arteries, the capillaries, and the veins in different colors; and
an image output interface configured to output and store a 3D subtraction MR arteriography image including only arteries, a 3D subtraction MR venography image including only veins, and a color-coded 4D MR angiography image.

7. The medical imaging system of claim 6, wherein the subtraction image processor comprises:
an MR arteriography subtractor configured to subtract venous phase signals from arterial phase signals for each pixel to create an arterial mask having a value greater than or equal to 0, and update an arterial phase MIP by multiplying the arterial phase MIP by the arterial mask to obtain 3D subtraction MR arteriography; and
an MR venography subtractor configured to subtract arterial phase signals from venous phase signals for each pixel to create a venous mask only having a value greater than or equal to 0, and update a venous phase MIP by multiplying the venous phase MIP by the venous mask to obtain 3D subtraction MR venography.

8. The medical imaging system of claim 6, wherein the color coding unit comprises a color weighting adjuster configured to allow arterial phase blood vessels from a time point when the arterial signal starts to rise to the arterial peak phase when the arterial signal intensity is greatest to be displayed in red, allow venous phase blood vessels from the venous peak phase when the venous signal intensity is greatest to a time point when the venous signal decreases to a plateau to be displayed in blue, allow blood vessels between the arterial peak phase and the venous peak phase to be displayed in green, and adjust color weightings of red, blue, and green in order to make blood vessels of a desired phase and hemodynamic change more visible, and set an optimal value that may vary depending on differences in MRI machines, imaging methods or contrast enhancement degrees.

9. The medical imaging system of claim 6, wherein the image output interface comprises:
a SUB MR arteriography image output interface configured to output and store grayscale and color 3D subtraction MR arteriography images;
a SUB MR venography image output interface configured to output and store grayscale and color 3D subtraction MR venography images;
a color-coded 4D MR angiography image output interface configured to output and store a color-coded 4D MR angiography image and a color-coded 3D MR angiography image; and
an image rotator configured to freely rotate an angiographic image about x, y, and z axes to obtain a projection in which a lesion or a specific blood vessel is well visible, or obtain continuous images rotated at a constant angle about the x and z axes.

* * * * *